(12) United States Patent
Klubben, III et al.

(10) Patent No.: US 12,311,064 B2
(45) Date of Patent: May 27, 2025

(54) ILLUMINATION OF LIGHT DIFFUSING OPTICAL FIBERS, ILLUMINATION OF BLUE-VIOLET LIGHT DELIVERY SYSTEMS, BLUE-VIOLET LIGHT DELIVERY SYSTEMS, AND METHODS FOR BLUE-VIOLET LIGHT INDUCED DISINFECTION

(71) Applicant: CORNING INCORPORATED, Corning, NY (US)

(72) Inventors: William Spencer Klubben, III, Boston, MA (US); Kaitlyn Matias Rees, Cambridge, MA (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 18/522,531

(22) Filed: Nov. 29, 2023

(65) Prior Publication Data

US 2024/0091393 A1 Mar. 21, 2024

Related U.S. Application Data

(62) Division of application No. 16/962,674, filed as application No. PCT/US2019/013733 on Jan. 16, 2019, now Pat. No. 11,850,314.

(Continued)

(51) Int. Cl.
*A61L 2/08* (2006.01)
*A61L 2/26* (2006.01)
*G02B 6/02* (2006.01)

(52) U.S. Cl.
CPC .............. *A61L 2/084* (2013.01); *A61L 2/26* (2013.01); *G02B 6/02395* (2013.01); *A61L 2202/11* (2013.01)

(58) Field of Classification Search
None
See application file for complete search history.

(56) References Cited

U.S. PATENT DOCUMENTS

| | | |
|---|---|---|
| 5,989,243 A | 11/1999 | Goldenberg |
| 6,551,346 B2 | 4/2003 | Crossley |

(Continued)

FOREIGN PATENT DOCUMENTS

| | | |
|---|---|---|
| CN | 1131646 A | 9/1996 |
| CN | 101272822 A | 9/2008 |

(Continued)

OTHER PUBLICATIONS

Machine translation of DE 102016009175 A1 provided by Clarivate, original document published 2017 (Year: 2017).*

(Continued)

*Primary Examiner* — Holly Kipouros
(74) *Attorney, Agent, or Firm* — Svetlana Z. Short

(57) ABSTRACT

A method of disinfecting using a light diffusing fiber includes optically coupling a light source to a light diffusing optical fiber having a core, a cladding surrounding the core, an outer surface, and a plurality of scattering structures positioned within the core, the cladding, or both the core and the cladding. The method further includes positioning the light diffusing optical fiber in optical engagement with a pathogen sample and directing light output by the light source into the light diffusing optical fiber for a first time interval. The scattering structures scatter light propagating along the light diffusing optical fiber toward the outer surface and a portion of the light diffuses through the outer surface thereby irradiating the pathogen sample with light having an average power density of about 5 $mW/cm^2$ to (Continued)

about 30 mW/cm² at a wavelength from about 380 nm to about 495 nm for an exposure time from about 2 hours to about 24 hours.

8 Claims, 14 Drawing Sheets

Related U.S. Application Data

(60) Provisional application No. 62/622,503, filed on Jan. 26, 2018, provisional application No. 62/617,784, filed on Jan. 16, 2018.

(56) References Cited

U.S. PATENT DOCUMENTS

| | | | |
|---|---|---|---|
| 7,450,806 | B2 | 11/2008 | Bookbinder et al. |
| 8,404,273 | B2 | 3/2013 | Baumgart et al. |
| 8,585,681 | B2 | 11/2013 | Boenig et al. |
| 8,591,087 | B2 | 11/2013 | Bickham et al. |
| 8,620,125 | B2 | 12/2013 | Button et al. |
| 8,779,386 | B2 | 7/2014 | Bak |
| 8,805,141 | B2 | 8/2014 | Fewkes et al. |
| 8,980,174 | B2 | 3/2015 | Haytman et al. |
| 9,039,966 | B2 | 5/2015 | Anderson et al. |
| 9,067,059 | B2 | 6/2015 | Bissig et al. |
| 9,259,513 | B2 | 2/2016 | Bedwell et al. |
| 9,439,989 | B2 | 9/2016 | Lalicki et al. |
| 9,550,005 | B2 | 1/2017 | Lin et al. |
| 9,795,466 | B2 | 10/2017 | Piergallini et al. |
| 9,808,647 | B2 | 11/2017 | Rhodes et al. |
| 9,925,390 | B2 | 3/2018 | Yehezkel |
| 9,943,379 | B2 | 4/2018 | Gregg et al. |
| 10,046,070 | B1 | 8/2018 | Lopez et al. |
| 10,166,402 | B2 | 1/2019 | Brennan et al. |
| 10,183,144 | B2 | 1/2019 | Tang et al. |
| 10,241,035 | B2 | 3/2019 | Bonnick et al. |
| 2005/0152146 | A1 | 7/2005 | Owen et al. |
| 2006/0085052 | A1 | 4/2006 | Feuerstein et al. |
| 2008/0254405 | A1 | 10/2008 | Montgomery et al. |
| 2009/0257910 | A1 | 10/2009 | Segal |
| 2010/0246169 | A1 | 9/2010 | Anderson et al. |
| 2010/0268151 | A1 | 10/2010 | Mauge et al. |
| 2013/0035629 | A1 | 2/2013 | Soltz et al. |
| 2013/0267888 | A1 | 10/2013 | Rhodes et al. |
| 2015/0080709 | A1 | 3/2015 | Chaturvedi |
| 2015/0144802 | A1 | 5/2015 | Bauco |
| 2015/0148734 | A1 | 5/2015 | Fewkes et al. |
| 2015/0182646 | A1 | 7/2015 | Anderson et al. |
| 2016/0015840 | A1 | 1/2016 | Gordon |
| 2016/0058937 | A1 | 3/2016 | Gaitas et al. |
| 2016/0271281 | A1 | 9/2016 | Clynne et al. |
| 2016/0354503 | A1 | 12/2016 | Hutchens et al. |
| 2018/0036443 | A1 | 2/2018 | Messerly |
| 2018/0147417 | A1 | 5/2018 | Rantala |
| 2018/0178031 | A1 | 6/2018 | Wu |
| 2018/0207302 | A1 | 7/2018 | Vasilenko |
| 2018/0304094 | A1 | 10/2018 | Hicks et al. |
| 2018/0326104 | A1 | 11/2018 | Hawkins et al. |
| 2019/0192879 | A1 | 6/2019 | Zaborsky |
| 2022/0323625 | A1 | 10/2022 | Stibich et al. |

FOREIGN PATENT DOCUMENTS

| | | | |
|---|---|---|---|
| CN | 104010710 | A | 8/2014 |
| CN | 104797518 | A | 7/2015 |
| CN | 204840698 | U | 12/2015 |
| CN | 105396169 | A | 3/2016 |
| CN | 106178280 | A | 12/2016 |
| CN | 106178282 | A | 12/2016 |
| CN | 106889157 | A | 6/2017 |
| CN | 106998764 | A | 8/2017 |
| CN | 108671243 | A | 10/2018 |
| EP | 1924323 | A1 | 5/2008 |
| EP | 2211914 | A1 | 8/2010 |
| EP | 2854944 | A1 | 4/2015 |
| JP | 11-038238 | A | 2/1999 |
| JP | 5546575 | B2 | 7/2014 |
| KR | 10-1362704 | B1 | 2/2014 |
| KR | 10-1784213 | B1 | 10/2017 |
| KR | 10-1851576 | B1 | 4/2018 |
| KR | 10-2018-0049757 | A | 5/2018 |
| KR | 10-1892996 | B1 | 8/2018 |
| KR | 10-2018-0135256 | A | 12/2018 |
| KR | 10-2018-0135257 | A | 12/2018 |
| SG | 11201407227 | R | 10/2017 |
| TW | 201707728 | A | 3/2017 |
| WO | 03/84601 | A2 | 10/2003 |
| WO | 2007/012875 | A1 | 2/2007 |
| WO | 2009/056838 | A1 | 5/2009 |
| WO | 2013/177674 | A1 | 12/2013 |
| WO | 2015/168129 | A1 | 11/2015 |
| WO | 2015/179472 | A1 | 11/2015 |
| WO | WO-2016154186 | A1 * | 9/2016 | ........... A61B 1/0653 |
| WO | 2017/062260 | A2 | 4/2017 |
| WO | 2017/205578 | A1 | 11/2017 |
| WO | 2018/009864 | A1 | 1/2018 |
| WO | 2019/025808 | A1 | 2/2019 |
| WO | 2019/027478 | A1 | 2/2019 |

OTHER PUBLICATIONS

Falcone et al., Effects of blue light on inflammation and skin barrier recovery following acute perturbation. Pilot study results in healthy human subjects, published onlineNov. 18, 2017, Photodermatol. Photoimmunol. Photomed. (Year: 2017).*
Zhang et al., Improvement of tellurium halide glasses for IR fiber optics, 1992, Journal of Non-Crystalline Solids, 140, pp. 47-51 (Year: 1992).*
Arecchi et al., Field Guide to Illumination, SPIE Press, 2007, p. 53 (Year: 2007).
Chinese Patent Application No. 201980011116.6, Office Action dated Sep. 28, 2021, 6 pages (English Translation Only), Chinese Patent Office.
Chinese Patent Application No. 201980011116.6, Office Action, dated Apr. 7, 2022, 22 pages (13 pages of English Translation and 9 pages of Original Document), Chinese Patent Office.
Document entitled JPH1138238A Optical Fiber Having Long Period Grating and Its Manufacturing Method, English machine translation of JPH1138238A provided by Espacenet, original document published 1999. (Year: 1999).
Endarko et al., "High-Intensity 405 nm Light Inactivation of Listeria monocytogenes," Photochem. Photobiol., 2012, 88(5):1280-1286.
Ganz et al., "Helicobacter pylori in Patients Can Be Killed by Visible Light," Lasers Surg. Med., 2005, 36(4):260-265.
Genina et al., "Adjunctive dental therapy via tooth plaque reduction and gingivitis treatment by blue light-emitting diodes tooth brushing," J. Biomed. Opt., 2015, 20(12):128004.
Gillespie et al., Efficacy of Pulsed 405-nm Light-Emitting Diodes for Antimicrobial Photodynamic Inactivation: Effects of Intensity, Frequency, and Duty Cycle, Oct. 19, 2016, Photomedicine and Laser Surgery, pp. 150-156 (Year: 2016).
Hessling et al., "Photoinactivation of bacteria by endogenous photosensitizers and exposure to visible light of different wavelengths—a review on existing data," FEMS Microbiol. Lett., 2017, 364(2):fnw270.
International Preliminary Report on Patentability of the International Searching Authority; PCT/US2019/013733; Mailed Jul. 30, 2020; 11 Pages; European Patent Office.
International Search Report and Written Opinion of the International Searching Authority; PCT/US2019/013733; Mailed Jun. 13, 2019; 13 Pages; European Patent Office.
Japanese Patent Application No. 2020-560117, Office Action dated Nov. 24, 2022, 6 pages (3 pages of English Translation and 3 pages of Original Document), Japanese Patent Office.
Jun-Shou Li, "Introduction to New Material", National Defense Industry Press, 2004, 6 pages (3 pages of English Translation and 3 pages of Original Document).

(56) References Cited

OTHER PUBLICATIONS

Maclean et al., "Inactivation of Bacterial Pathogens following Exposure to Light from a 405-Nanometer Light-Emitting Diode Array," Appl. Environ. Microbiol., 2009, 75(7):1932-1937.
Murdoch et al., "Bactericidal Effects of 405?nm Light Exposure Demonstrated by Inactivation of *Escherichia, Salmonella, Shigella, Listeria*, and *Mycobacterium* Species in Liquid Suspensions and on Exposed Surfaces," Scientific World Journal, 2012; 2012: 137805.
Murdoch et al., "Lethal effects of high-intensity violet 405-nm light on *Saccharomyces cerevisiae*, Candida albicans, and on dormant and germinating spores of Aspergillus niger," Fungal Biol., 2013, 117(7-8):519-527.
Rhodes et al., "Violet 405 nm Light: A Novel Therapeutic Agent Against (Beta)-Lactam-Resistant *Escherichia coli*," Lasers Surg. Med., 2016, 48(3):311-317.
RP Photonics Encyclopedia, "Polarization of Laser Emission", webpage cached Feb. 12, 2017 by Internet Archive (Year: 2017).
Taiwanese Patent Application No. 108101626, Office Action dated Dec. 8, 2022, 2 pages (English Translation Only); Taiwanese Patent Office.

\* cited by examiner

ILLUMINATION OF LIGHT DIFFUSING OPTICAL FIBERS, ILLUMINATION OF BLUE-VIOLET LIGHT DELIVERY SYSTEMS, BLUE-VIOLET LIGHT DELIVERY SYSTEMS, AND METHODS FOR BLUE-VIOLET LIGHT INDUCED DISINFECTION

CROSS-REFERENCE TO RELATED APPLICATIONS

This application is a divisional of U.S. application Ser. No. 16/962,674 filed Jul. 16, 2020, which claims the benefit of priority under 35 U.S.C § 371 of International Application No.: PCT/US2019/013733 filed on Jan. 16, 2019, which claims the benefit of priority under 35 U.S.C. § 119 of U.S. Provisional Application Ser. No. 62/617,784 filed on Jan. 16, 2018 and of U.S. Provisional Application Ser. No. 62/622,503 filed on Jan. 26, 2018, the contents of which are relied upon and incorporated herein by reference in their entirety.

TECHNICAL FIELD

The present disclosure generally relates to illumination of light diffusing optical fibers, illumination of blue-violet light delivery systems, blue-violet light delivery systems, and methods for blue-violet light induced disinfection using the same. More specifically, the present disclosure relates to light diffusing optical fibers and other delivery systems for delivering blue-violet light to blue-violet light induced disinfection applications.

BACKGROUND

There are approximately 722,000 cases of hospital acquired infections (HAIs), which result in about 75,000 deaths per year in the United States alone (according to U.S. Center for Disease Control statistics). Additionally, these cases cost the U.S. healthcare system 15-30 billion dollars per year because the hospitals are not reimbursed for HAIs. Current treatments for HAIs are largely antibiotic-based, which are becoming less effective due to the increase of multidrug resistant pathogens and the decrease in new antibiotic drugs on the market and in regulatory testing stages.

One source of HAIs is believed to be medical devices such as Foley catheters, Endotracheal tubes, Cardio vascular catheters, endoscopes, abscess draining catheters, dialysis catheters, ports, etc., can become infected themselves before, after and during use. High intensity blue-violet light can be used to kill microbes that grow on such medical devices to prevent the medical devices themselves from being transmitters or the source of infections. There is a need for delivering such blue-violet light to these medical devices and other sources of HAIs in vivo, ex vivo or both in vivo and ex vivo.

Optical fibers are used for a variety of applications where light needs to be delivered from a light source to a remote location. Optical telecommunication systems, for example, rely on a network of optical fibers to transmit light from a service provider to system end-users.

Telecommunication optical fibers are designed to operate at near-infrared wavelengths in the range from 800 nm to 1675 nm where there are only relatively low levels of attenuation due to absorption and scattering. This allows most of the light injected into one end of the fiber to exit the opposite end of the fiber with only insubstantial amounts exiting peripherally through the sides of the fiber.

Because optical fibers are typically designed to efficiently deliver light from one end of the fiber to the other end of the fiber over long distances, very little light escapes from the sides of the typical fiber, and, therefore optical fibers are not considered to be well-suited for use in forming an extended illumination source. Yet, there are a number of applications such as special lighting, signage, or biological applications, including disinfecting materials, surfaces and even medical equipment, where select amounts of light need to be provided in an efficient manner to the specified areas. For biological applications there is a need to develop light delivery systems and processes for disinfecting materials, surfaces, medical devices and equipment, and organic mediums of pathogens. Such the light delivery systems need to be thin, flexible, and easily modified to variety of different shapes and illumination paths to for hard to reach areas with compound shapes, such as open wounds or the length of a cardiovascular catheter, endotracheal tube, a Foley catheter, or the like.

Accordingly, a need exists for guiding and scattering light propagating along the light delivery system, such as a light diffusing optical fiber, for blue-violet light induced disinfection applications.

BRIEF SUMMARY

According to the subject matter of the present disclosure, a method of disinfecting using a light diffusing fiber includes optically coupling a light source to one or more light diffusing optical fibers having a core, a cladding surrounding the core, an outer surface, and a plurality of scattering structures positioned within the core, the cladding, or both the core and the cladding. The method further includes positioning the one or more light diffusing optical fibers in optical engagement with a pathogen sample and directing light output by the light source into the one or more light diffusing optical fibers for a first time interval. The scattering structures of the one or more light diffusing optical fibers scatter light propagating along the one or more light diffusing optical fibers toward the outer surface and a portion of the light diffuses through the outer surface thereby irradiating the pathogen sample with light having an average power density of about 5 $mW/cm^2$ to about 30 $mW/cm^2$ at a wavelength from about 380 nm to about 495 nm for an exposure time from about 30 minutes to about 48 hours.

In accordance with another embodiment of the present disclosure, a method of disinfecting using a light diffusing optical fiber including optically coupling a light source to a light diffusing optical fiber having a core, a cladding surrounding the core, an outer surface, and a plurality of scattering structures positioned within the core, the cladding, or both the core and the cladding. The method further includes positioning one or more light diffusing optical fibers in optical engagement with a pathogen sample and directing light output by the light source into the one or more light diffusing optical fibers for a first time interval. The scattering structures of the one or more light diffusing optical fibers scatter light propagating along the one or more light diffusing optical fibers toward the outer surface and a portion of the light diffuses through the outer surface thereby irradiating the pathogen sample having an amount of colony forming units with light comprising an average power density of about 5 $mW/cm^2$ to about 30 $mW/cm^2$ at a wavelength from about 380 nm and about 495 nm, where the amount of colony forming units of the pathogen sample are reduced by about a 4-Log reduction to about a 9-Log reduction.

Although the concepts of the present disclosure are described herein with primary reference to light diffusing optical fibers with uniform illumination along the length, it is contemplated that the concepts will enjoy applicability to any light diffusing optical fiber.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
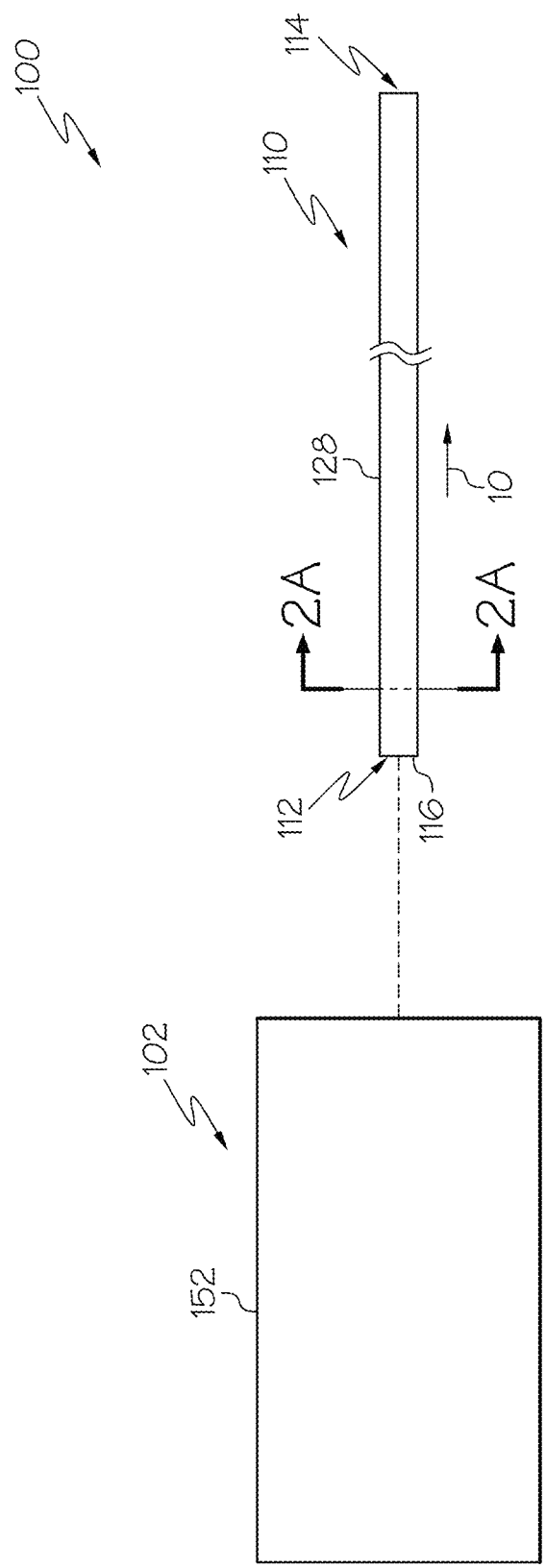
FIG. 1 schematically depicts an illumination system comprising a light output device and a light diffusing optical fiber, according to one or more embodiments shown and described herein.

Various aspects of this disclosure pertain to blue-violet light delivery systems that delivery blue-violet light at relatively low power densities that enable the reduction of common pathogens in relatively short periods of time. Without being bound by theory, such light delivery systems are believed to be less harmful than ionizing light (such as ultraviolet light) because it does not damage tissue and DNA. Such light is also believed to be less prone to resistance than antibiotics because it is not chemically based. Moreover, the light delivery systems described herein can be inertly integrated into a medical device or catheter to provide blue-violet light illumination in the most critical and hard to reach areas. Further, the light delivery system and the blue-violet light can be applied to a targeted site and provide continual disinfection unlike other systemic antibiotics or site-specific treatments/prevention techniques which eventually become ineffective. The light delivered by the light delivery system can also be administered prophylactically (i.e. to prevent getting the HAI in the first place) during the treatments known to lead to infections. Without being bound by theory, it is believed that broad spectrum kill can be achieved and can be administered immediately such that a patient does not have to wait for days to determine the identity of microbe causing the infection before beginning drug-specific treatment or endure treatment using a variety of antibiotics because the microbe is unknown. Moreover, the light delivery system can direct the treat to the point of infection, without subjecting the entire body to the treatment (which may have undesirable side-effects).

A first aspect of this disclosure pertains to methods of disinfecting using a blue-violet light delivery system. In one or more embodiments, the system comprises a light diffusing optical fiber and an optional light source that delivers blue-violet light that has an average power density of about 5 mW/cm$^2$ to about 30 mW/cm$^2$ at a wavelength from about 380 nm to about 495 nm. In one or more embodiments, the light delivery system can continuously deliver light and thus energy to the infection site. In one or more embodiments, the light delivered reduces the colony forming units of a pathogen that is irradiated by 4-Log reduction over a relatively short period of time (e.g., 6 hours or less).

Referring generally to the figures, one or more embodiments of a light diffusing optical fiber that can be used in the light delivery system comprises a core, a cladding surrounding the core, an outer surface and a plurality of scattering structures positioned within the core, the cladding, or both the core and the cladding. In operation, when light is directed into the light diffusing optical fiber the scattering structures of the light diffusing optical fiber scatter light propagating along the light diffusing optical fiber toward the outer surface and a portion of the light diffuses through the outer surface. Additionally, the figures generally refer to methods of disinfecting using a light diffusing optical fiber include optically coupling a light source to a light diffusing optical fiber, positioning the light diffusing optical fiber in optical engagement with a pathogen sample, and directing light output by the light source into the light diffusing optical fiber for a time interval thereby irradiating the pathogen sample with light comprising an average power density at a wavelength for an exposure time.

Figure 2A:
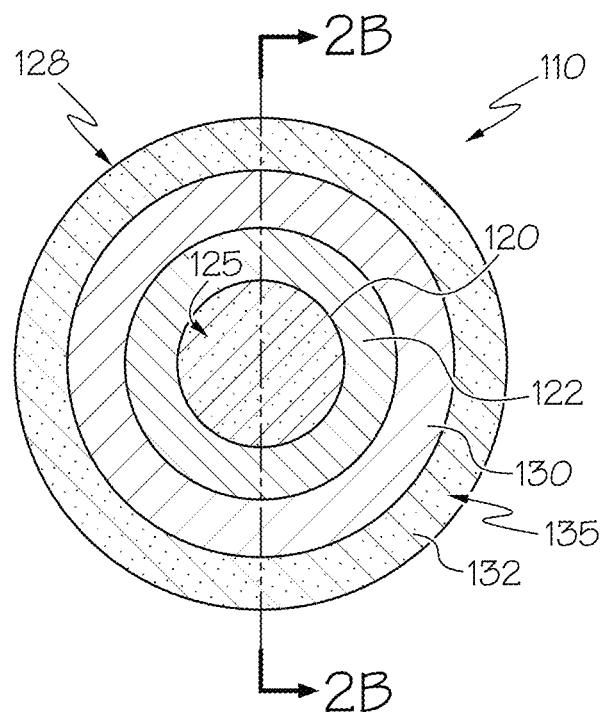
FIG. 2A schematically depicts a cross section of a light diffusing optical fiber, according to one or more embodiments shown and described herein.
Figure 2B:
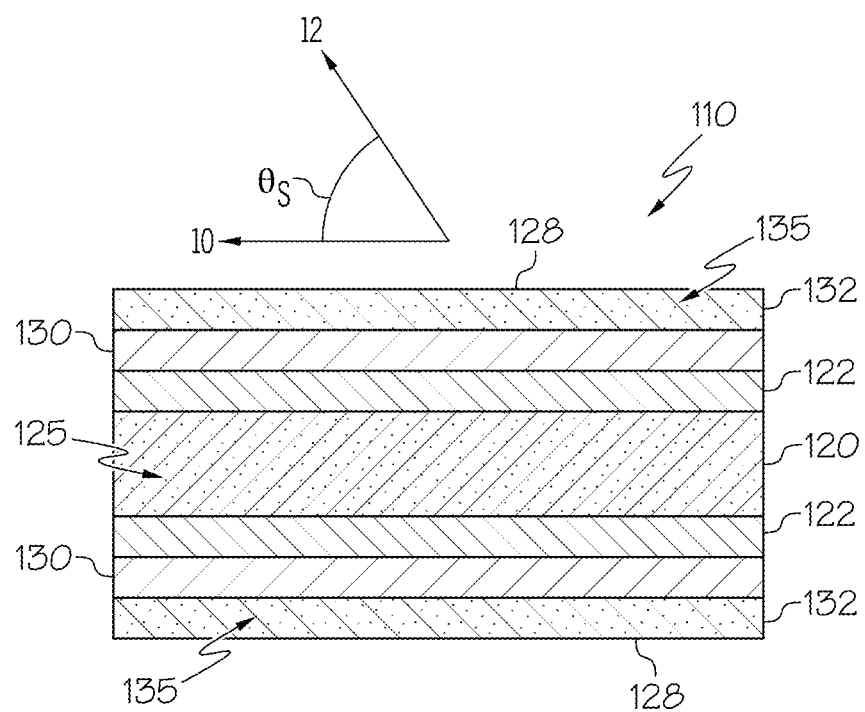
FIG. 2B schematically depicts a cross section of the light diffusing optical fiber of FIG. 2A, according to one or more embodiments shown and described herein.
Figure 3A:
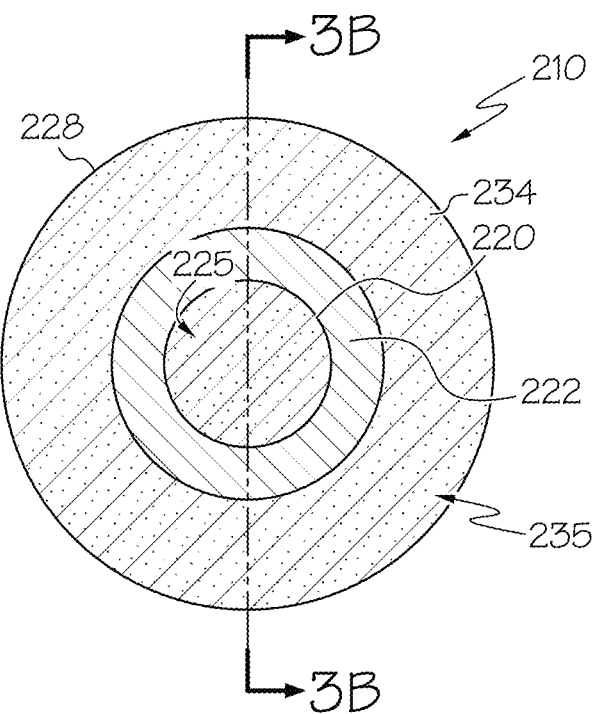
FIG. 3A schematically depicts a cross section of another embodiment of a light diffusing optical fiber, according to one or more embodiments shown and described herein.
Figure 3B:
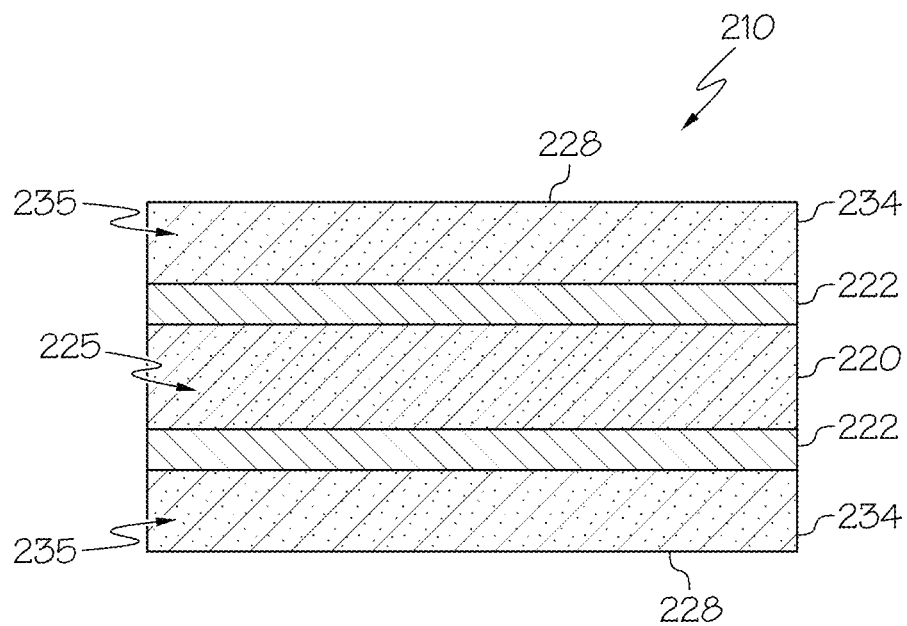
FIG. 3B schematically depicts a cross section of the light diffusing optical fiber of FIG. 3A, according to one or more embodiments shown and described herein.
Figure 4A:
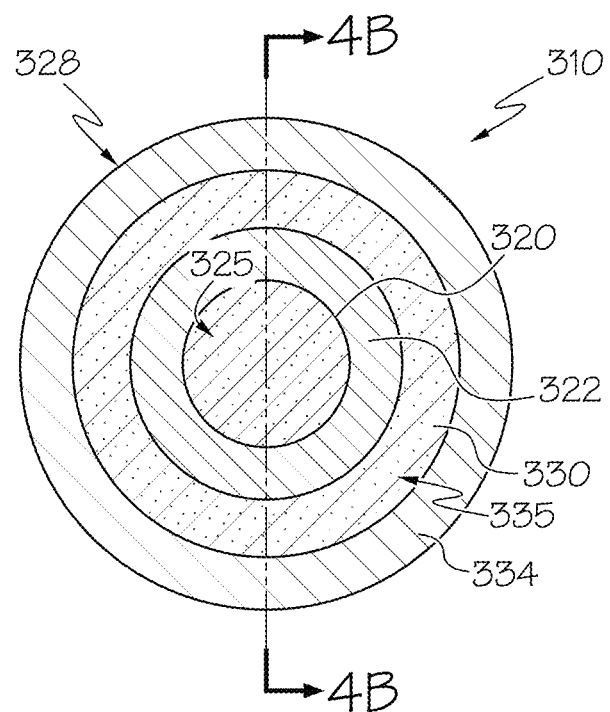
FIG. 4A schematically depicts a cross section of another embodiment of a light diffusing optical fiber, according to one or more embodiments shown and described herein.
Figure 4B:
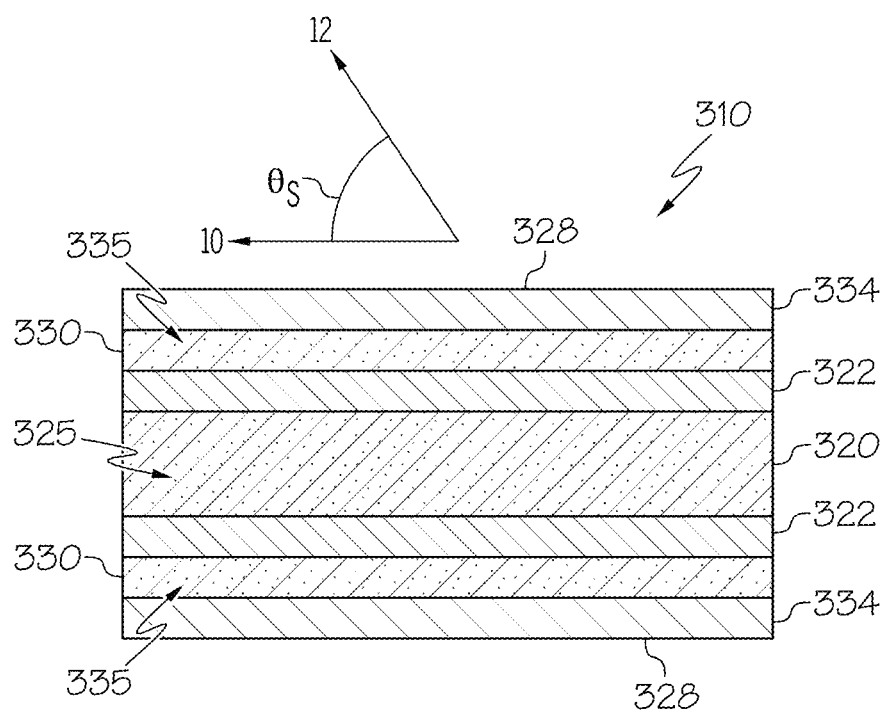
FIG. 4B schematically depicts a cross section of the light diffusing optical fiber of FIG. 4A, according to one or more embodiments shown and described herein.

Referring now to FIG. 1, an illumination system 100 comprises a light diffusing optical fiber 110 optically coupled to a light output device 102 that includes a light source 152. The light diffusing optical fiber 110 comprises a first end 112, a second end 114 opposite the first end 112. Cross sections of embodiments of the light diffusing optical fiber are depicted in FIGS. 2A-4C. For example, FIGS. 2A and 2B depict cross sections of the light diffusing optical fiber 110, FIGS. 3A and 3B depict cross sections of a light diffusing optical fiber 210, and FIGS. 4A and 4B depict cross sections of a light diffusing optical fiber 310. Each light diffusing optical fiber 110, 210, 310 described herein comprises a core 120, 220, 320, a cladding 122, 222, 322 surrounding the core 120, 220, 320, an outer surface 128, 228, 328, and a plurality of scattering structures 125, 225, 325 positioned within the core 120, 220, 320, the cladding 122, 222, 322, or both the core 120, 220, 320 and the cladding 122, 222, 322.

As used herein, the "outer surface" 128, 228, 328 refers to the outermost surface of the light diffusing optical fiber 110, 210, 310. In the embodiments depicted in FIGS. 2A and 2B, the outer surface 128 is a surface of a secondary polymer coating layer 132, in the embodiments depicted in FIGS. 3A and 3B, the outer surface 228 is a surface of a thermoplastic polymer coating layer 234, and in the embodiments depicted in FIGS. 4A and 4B, the outer surface 328 is a surface of a thermoplastic polymer coating layer 334. However, while the embodiments depicted in FIGS. 2A-4B include a secondary polymer coating layer 132, a thermoplastic polymer coating layer 234, and a thermoplastic polymer coating layer 334, respectively, in some embodiments, the light diffusing optical fiber may not include the secondary polymer coating layer 132, the thermoplastic polymer coating layer 234, and the thermoplastic polymer coating layer 334 such that the outer surface 128, 228, and 328 may be a surface of the cladding 122, 222, 322, respectively. Further, the plurality of scattering structures 125, 225, 325 are configured to scatter guided light (e.g., light output by the light output device 102 that is propagating along the light diffusing optical fiber 110, 210, 310) toward the outer surface 128, 228, 328 of the light diffusing optical fiber 110, 210, 310 such that a portion of the guided light diffuses through the outer surface 128 along a diffusion length of the light diffusing optical fiber 110, 210, 310. Further, the light diffusing optical fiber 110, 210, 310 will may comprise a length (e.g., a length between the first end 112 and the second end 114) of from about 0.15 m to about 100 m, for example, about 100 m, 75 m, 50 m, 40 m, 30 m, 20 m, 10 m, 9 m, 8 m, 7 m, 6 m, 5 m, 4 m, 3 m, 2 m, 1 m, 0.75 m, 0.5 m, 0.25 m, 0.15 m, or 0.1 m.

As used herein, "diffusion length," is the length of the light diffusing optical fiber 110 extending from the first end 112 of the light diffusing optical fiber 110 (or from any end receiving input light) to a location along the length of the light diffusing optical fiber 110 where 90% of the guided light has diffused from the light diffusing optical fiber 110. As used herein, the term "light-diffusing" means that light scattering is substantially spatially continuous along at least a portion of the length of the light diffusing optical fiber 110, i.e., there are no substantial jumps or discontinuities such as those associated with discrete (e.g., point) scattering. Thus, the concept of substantially continuous light emission or substantially continuous light scattering as set forth in the present disclosure refers to spatial continuity. Further, as used herein, "uniform illumination" refers to illumination along the length of the light diffusing optical fiber 110 in which the intensity of light emitted from the light diffusing optical fiber 110 does not vary by more than 25% over the specified length. It should be understood that the above definitions also apply to the light diffusing optical fibers 210, 310 of FIGS. 2A-4B.

Referring again to FIG. 1, the light output device 102 is optically coupled to the first end 112 of the light diffusing optical fiber 110 (or in other embodiments, the light diffusing optical fibers 210 or 310) such that light output by the light source 152 of the light output device 102 may irradiate the end face 116 of the first end 112 of the light diffusing optical fiber 110 and enter the light diffusing optical fiber 110. The light source 152 may comprise a light-emitting diode (LED), a laser diode, or the like. For example, the light source 152 may comprise a multimode laser diode, single mode laser diode, a SiP laser diode, a VCSEL laser diode, or another type of semiconductor laser diode. Further, the light source 152 may be linearly polarized. Optionally, the light source may be a laser light which is polarized and coherent. Further, the light source 152 may be configured to generate light in the 200 nm to 2000 nm wavelength range.

In some embodiments, the light source 152 may be configured to generate light in the 200 nm to 2000 nm wavelength range. For example, the light source 152 may be an ultraviolet (UV) or a visible, blue-violet light source configured to emit light at a wavelength of from about 200 nm to about 500 nm, for example, about 225 nm, 250 nm, 275 nm, 300 nm, 325 nm, 350 nm, 375 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, or the like, such as about 300 nm to about 460 nm or about 400 nm to about 495 nm. The light output device 102 may further comprise additional optical components such as a lens, an optical delivery fiber, or the like, positioned between and optically coupled to the light source 152 and the first end 112 of the light diffusing optical fiber 110 to facilitate the input of light into the light diffusing optical fiber 110. Moreover, these additional optical components, such as an optical delivery fiber, may allow the light source 152 to be spatially separated from the light diffusing optical fiber 110.

In operation, because light emitted by the light source 152 is scattered into the surrounding environment by the light diffusing optical fiber 110, the light source 152 may be positioned at a location remote from the light diffusing optical fiber 110. Accordingly, any thermal heat generated by the light source 152 may be transferred away from the light source 152 to locations remote from both the light source 152 and the light diffusing optical fiber 110. Thus, the temperature of the light diffusing optical fiber 110 may remain substantially similar to the ambient temperature of the surrounding environment and the lighting unit may be described as a thermally "cool" lighting unit. Further, spatially separating the light diffusing optical fiber 110 and the light source 152 may provide additional design flexibility to the illumination system 100.

Referring now to FIGS. 2A-4B, each of the light diffusing optical fibers 110, 210, 310, are configured to induce scattering through the outer surface 128, 228, 328 with a high scattering efficiency, in particular, when the guided light propagating along the length of the light diffusing optical fiber 110, 210, 310 comprise wavelengths in the ultraviolent range (e.g., from about 200 nm to about 500 nm). As used herein, "scattering efficiency" refers to the percentage of light scattering outward from the core 120, 220, 320 of the light diffusing optical fiber 110, 210, 310 towards the outer surface 128, 228, 328 that in not absorbed, blocked, or otherwise lost, and in fact exits the outer surface 128, 228, 328. While not intending to be limited by theory, a percentage of light scattering from the core 120, 220, 320 may be absorbed by the one or more additional layers of the light diffusing optical fiber 110, 210, 310 surrounding the cladding 122, 222, 322. However, the light diffusing optical fibers 110, 210, 310 described herein limit absorption of UV light and visible, blue-violet light scattering through the outer surface 128, 228, 328 and facilitate high scattering efficiency at UV and visible, blue-violet wavelengths.

Referring still to FIGS. 2A-4B, the core 120, 220, 320 and the cladding 122, 222, 322 of each of the light diffusing optical fibers 110, 210, 310 may comprise a glass, such as silica glass, doped with a hydroxyl material (e.g., a hydroxyl doped glass core and a hydroxyl doped glass cladding). As used herein, "hydroxyl doped" refers to a glass comprising 300 ppm or more of a hydroxyl material, for example hydroxyl ions (OH), excess oxygen (which may be added to the glass), or the like. While not intending to be limited by theory, doping the core 120, 220, 320 and the cladding 122, 222, 322 with a hydroxyl material may be advantageous at UV and visible, blue-violet wavelengths. While glass cores and claddings having a low hydroxyl content (e.g., hydroxyl content of less than 300 ppm) have increased transmissivity at higher wavelengths (e.g., wavelengths in the visible range, near infrared (NIR) range, and infrared range), they also incur increased absorption losses at wavelengths in the UV and visible, blue-violet range because lowering the hydroxyl content in the glass increases the number and/or size of oxygen deficiency centers in the glass. As used herein, "oxygen deficiency center" refers to formation of broken bonds of silica having an oxygen vacancy. While not intending to be limited by theory, oxygen deficiency centers in the core 120, 220, 320 and the cladding 122, 222, 322 absorb light comprising a wavelength in the UV and visible, blue-violet range, which darkens the core 120, 220, 320 and the cladding 122, 222, 322 and reduces the percentage of light scattered outward from the core 120, 220, 320 by the scattering structures 125, 225, 325 that diffuses through the outer surface 128, 228, 328 of the light diffusing optical fiber 110, 210, 310. While not intending to be limited by theory, under UV and visible, blue-violet radiation, different "color centers" can be developed in fused silica. The origin of a color center may be related to ionization of the fused silica. While still not intending to be limited by theory, color centers may react with OH to form stable non-absorbing species. In some embodiments, the light diffusing optical fiber 110, 210, 310 may be hydroxyl doped by hydrogen loading the silica of the light diffusing optical fiber 110, 210, 310 with high pressure and temperature.

Moreover, while not intending to be limited by theory, some polymer materials, such as some UV curable polymers, are highly absorptive of UV light and visible, blue-violet light. Thus, it is advantageous to limit the number and thickness of polymer layers of the light diffusing optical fiber 110, 210, 310 and use polymer layers with limited absorption of UV light and visible, blue-violet light. For example, in each embodiment depicted in FIGS. 2A-4B, the cladding 122, 222, 322 comprises glass (e.g., hydroxyl doped glass). Further, each of the embodiments of the light diffusing optical fiber 110, 210, 310 described herein comprise at least one polymer layer surrounding the cladding 122, 222, 322, however, as described in more detail below, each of these polymer layers comprise low absorption of UV light and visible, blue-violet light.

Referring now to FIGS. 2A and 2B, cross sections the light diffusing optical fiber 110 comprising the core 120, the cladding 122 surrounding the core 120, the outer surface 128 and the plurality of scattering structures 125 are depicted. The core 120 comprises a glass core (e.g., silica) doped with a hydroxyl material (e.g., silica comprising about 300 ppm or more of a hydroxyl material). The cladding 122 comprises a glass cladding (e.g., F-doped silica or F (fluorine)/B (boron) co-doped silica having a lower refractive index than the refractive index of the core 120) doped with a hydroxyl material (e.g., F-doped silica or F (fluorine)/B (boron) co-doped silica comprising about 300 ppm or more of a hydroxyl material). The light diffusing optical fiber 110 further comprises a primary polymer coating 130 surrounding the cladding 122 and the secondary polymer coating layer 132 surrounding the primary polymer coating 130.

Referring still to FIGS. 2A and 2B, the scattering structures 125 may occur throughout the core 120 (as depicted in FIGS. 2A and 2B), or may occur near the interface of the core 120 and the cladding 122 (e.g., the core-cladding boundary), or may occur in an annular ring within the core 120. The scattering structures 125 may comprise gas filled voids, scattering particles, such as ceramic materials, dopants, or the like. Some examples of light-diffusing optical fibers having randomly arranged and randomly sized voids (also referred to as "random air lines" or "nanostructures" or "nano-sized structures") are described in U.S. Pat. No. 7,450,806, and in U.S. patent application Ser. Nos. 12/950,045, 13/097,208, and 13/269,055, herein incorporated by reference in their entirety. Alternatively, the light diffusing optical fiber 110 may have a "roughened" core 120, where the irregularities on the surface of the core 120 at the core-cladding boundary causes light scatter. Other types of light diffusing optical fibers may also be utilized. In operation, the light diffusing optical fiber 110 may undergo scattering-induced attenuation (i.e., attenuation due to light lost through the outer surface 128 of the light diffusing optical fiber 110, not due to absorption of scattering particles within the light diffusing optical fiber 110) about 50 dB/km or greater, for example from about 100 dB/km to about 60000 dB/km at an illumination wavelength (e.g., the wavelength(s) of emitted radiation).

In embodiments in which the scattering structures 125 comprise gas filled voids, the gas filled voids may be arranged in a random or organized pattern and may run parallel to the length of the light diffusing optical fiber 110 or may be helical (i.e., rotating along the long axis of the light diffusing optical fiber 110). Further, the light diffusing optical fiber 110 may comprise a large number of gas filled voids, for example more than 50, more than 100, or more than 200 voids in the cross section of the fiber. The gas filled voids may contain, for example, $SO_2$, Kr, Ar, $CO_2$, $N_2$, $O_2$, or mixtures thereof. However, regardless of the presence or absence of any gas, the average refractive index in region of the core 120, the cladding 122, or the core-cladding boundary that comprises the plurality of scattering structures 125 is lowered due to the presence of voids. Further, the plurality of scattering structures 125 such as voids can be randomly or non-periodically disposed in the core 120, the cladding 122, or the core-cladding boundary, however, in other embodiments the voids may be periodically disposed.

The cross-sectional size (e.g., diameter) of the voids, such as gas filled voids (or other scattering particles) may be from about 10 nm to about 10 μm and the length may vary from about 1 μm to about 50 m. In some embodiments, the cross sectional size of the voids (or other scattering particles) is about 10 nm, 20 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 1 μm, 2 μm, 3 μm, 4 μm, 5 μm, 6 μm, 7 μm, 8 μm, 9 μm, or 10 μm. In some embodiments, the length of the voids is about 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μ2m, 300 μm, 400 μm, 500 μm, 600 μm, 700 μm, 800 μm, 900 μm, 1000 μm, 5 mm, 10 mm, 50 mm, 100 mm, 500 mm, 1 m, 5 m, 10 m, 20 m, or 50 m.

Referring still to FIGS. 2A and 2B, the primary polymer coating 130 may comprise a substantially clear layer surrounding the core 120 and cladding 122 for ease of mechanical handling, for example, a polymer coating. Further, the secondary polymer coating layer 132 may be positioned surrounding the core 120, the cladding 122, and the primary polymer coating 130. The secondary polymer coating layer 132 operates as a scattering layer and comprises a base material (for example, a polymer) and a plurality of scattering particles 135 positioned in the base material. In operation, the secondary polymer coating layer 132 may facilitate uniform angular scattering over a large angular range (e.g., 40 to 120°, or 30° to 130°, or 15 to 150°). For example, the light diffusing optical fiber 110 is configured to provide substantially uniform illumination due to scattering, such that the difference between the minimum and maximum scattering illumination intensity is less than 50% of the maximum scattering illumination intensity, for all viewing angles between 40 and 120 degrees.

The scattering particles 135 comprise a refractive index differential from the base material of the secondary polymer coating layer 132 (e.g. a base polymer having a refractive index of about 1.5) of more than 0.05 (e.g., the difference in refractive indices between the base material and each scattering particle 135 is greater than 0.05). In some embodiments, the difference in refractive indices between the base material and the each scattering particle 135 is at least 0.1. That is, the index of refraction of each scattering particle 135 may be at least 0.1 larger than the index of refraction of the base material (e.g., of the polymer or other matrix material) of the secondary polymer coating layer 132. Further, to limit the absorption of UV light and visible, blue-violet light traversing the secondary polymer coating layer 132, the scattering particles 135 comprise a material having low absorbance of UV light and visible, blue-violet light (e.g., low absorption scattering materials). Example low absorption materials scattering materials having a refractive index greater than the base material (e.g., greater than about 1.5) include aluminum oxide ($Al_2O_3$) having a refractive index of about 1.77, barium sulfate ($BaSO_4$) having a refractive index of about 1.636, gas voids such as microbubbles with refractive index of about 1, or the like. Further, in some embodiments, the scattering particles 135 may instead or in addition comprise gas voids or microbubbles.

Further, the cross-sectional size of each scattering particle 135 within the secondary polymer coating layer 132 may comprise 0.1λ to 10λ, where λ is the wavelength of light propagating through the light diffusing optical fiber 110. In some embodiments, the cross-sectional size of each scattering particle 135 is greater than 0.2λ and less than 5λ, for example, between 0.5λ and to 2λ. For example, the cross-sectional size of each scattering particle may comprise from about 20 nm to about 5 μm, for example, about 50 nm, 75 nm, 100 nm, 150 nm, 200 nm, 350 nm, 400 nm, 450 nm, 500 nm, 550 nm, 600 nm, 650 nm, 700 nm, 750 nm, 800 nm, 850 nm, 900 nm, 950 nm, 1 μm, 1.1 μm, 1.2 μm, 1.3 μm, 1.4 μm, 1.5 μm, 1.6 μm, 1.7 μm, 1.8 μm, 1.9 μm, 2 μm, 2.1 μm, 2.2 μm, 2.3 μm, 2.4 μm, 2.5 μm, 2.6 μm, 2.7 μm, 2.8 μm, 2.9 μm, 3 μm, 3.1 μm, 3.2 μm, 3.3 μm, 3.4 μm, 3.5 μm, 3.6 μm, 3.7 μm, 3.8 μm, 3.9 μm, 4 μm, 4.1 μm, 4.2 μm, 4.3 μm, 4.4 μm, 4.5 μm, 4.6 μm, 4.7 μm, 4.8 μm, 4.9 μm, or the like. Further, the scattering particles 135 in the secondary polymer coating layer 132 may comprise from about 0.005% to 70% by weight of the secondary polymer coating layer 132, for example, 0.01% to 60%, 0.02% to 50%, or the like.

In some embodiments, the plurality of scattering particles 135 may be disposed within a sublayer of the secondary polymer coating layer 132. For example, in some embodiments, the sublayer may have a thickness of about 1 μm to about 5 μm. In other embodiments, the thickness of the particle sublayer and/or the concentration of the scattering particles 135 in the secondary polymer coating layer 132 may be varied along the axial length of the light diffusing optical fiber 110 so as to provide more uniform variation in the intensity of light scattered from the light diffusing optical fiber 110 at large angles (i.e., angles greater than about 15 degrees). For example, the angular illumination for all viewing angles between 40 and 120 degrees is within 50% of maximum illumination, and in some embodiments within 30%. In some embodiments, the angular illumination for all viewing angles between 40 and 120 degrees is within 30% of maximum illumination, and in some embodiments within 25%.

Referring now to FIGS. 3A and 3B, cross sections the light diffusing optical fiber 210 comprising the core 220, the cladding 222 surrounding the core 220, scattering structures 225 and a thermoplastic polymer coating layer 234 surrounding and contacting the cladding 222 are depicted. The core 220 comprises a glass core (e.g., silica) doped with a hydroxyl material (e.g., silica comprising about 300 ppm or more of a hydroxyl material). The cladding 222 comprises a glass cladding (e.g., F-doped silica or F (fluorine)/B (boron) co-doped silica having a lower refractive index than the refractive index of the core 220) doped with a hydroxyl material (e.g., doped silica or F (fluorine)/B (boron) co-doped silica comprising about 300 ppm or more of a hydroxyl material). The scattering structures 225 may occur throughout the core 220 (as depicted in FIGS. 3A and 3B), or may occur near the interface of the core 220 and the cladding 222 (e.g., the core-cladding boundary), or may occur in an annular ring within the core 220. The scattering structures 225 may comprise any of the scattering structures 125 described above with respect to the light diffusing optical fiber 110, for example, gas filled voids, scattering particles, such as ceramic materials, dopants, or the like.

The thermoplastic polymer coating layer 234 comprises a fluorinated polymer material such as polytetrafluoroethylene (PTFE), such as Teflon™, ethylene-tetrafluoroethylene (ETFE), such as Tefzel™, polyethylene terephthalate (PET), fluorinated ethylene propylene (FEP), perfluoroalkoxy alkane (PFA), PEEK (polyetheretherketone), Nylon, and any other fluorinated extrudable polymer. The thermoplastic polymer coating layer 234 comprises low absorbance of UV light and visible, blue-violet light (as described in more detail with respect to graph 50 of FIG. 5, below) and is a hard plastic material, which provides a protective coating layer surrounding the core 220 and the cladding 222. In the embodiment depicted in FIGS. 3A and 3B, the thermoplastic polymer coating layer 234 is in direct contact with the cladding 222 and thus, no intervening layers are positioned between the cladding 222 and the thermoplastic polymer coating layer 234, limiting the amount of UV light and visible, blue-violet light scattering outward from the core 220 towards the outer surface 228 that is absorbed, blocked or otherwise prevented from exiting the outer surface 228.

Further, as depicted in FIGS. 3A and 3B, scattering particles 235 are disposed in the thermoplastic polymer coating layer 234. The scattering particles 235 disposed within the thermoplastic polymer coating layer 234 may comprise any of the scattering particles 135 described above with respect to the light diffusing optical fiber 110. The thermoplastic polymer coating layer 234 may comprise a refractive index of from about 1.30 to about 1.35. The scattering particles 235 may comprise low absorption scattering materials having a refractive index greater than the refractive index of the thermoplastic polymer coating layer 234, for example, $Al_2O_3$ having a refractive index of about 1.77, $BaSO_4$ having a refractive index of about 1.636, silicon dioxide ($SiO_2$) having a refractive index of about 1.46, or the like. Note that because the thermoplastic polymer coating layer 234 comprises a refractive index that is lower than the secondary polymer coating layer 132, materials may be used as scattering particles 235 that are not available as scattering particles 135. In particular, $SiO_2$ may be used as a material of scattering particles 235, which may be advantageous because $SiO_2$ is transparent to light having a wavelength of about 200 nm and greater, thereby reducing absorption loss caused by the scattering particles 235 in the UV and visible, blue-violet range. Further, in some embodiments, the scattering particles 235 may instead or in addition comprise gas voids or microbubbles.

In some embodiments, the thermoplastic polymer coating layer 234 may be applied directly to the cladding 222 of the light diffusing optical fiber 210 during a fiber draw process. For example, while not intending to be limited by theory, the core 220 and the cladding 222 may be drawn from an optical fiber preform, though a draw furnace, which heats the optical fiber preform, and a fiber coating unit, which applies the thermoplastic polymer coating layer 234 to the cladding 222 of the light diffusing optical fiber 210. Further, after the thermoplastic polymer coating layer 234 is applied, the light diffusing optical fiber 210 reaches a fiber collection unit, which may comprise one or more drawing mechanisms and tensioning pulleys to provide tension to the light diffusing optical fiber 210 and facilitate winding the light diffusing optical fiber 310 onto a fiber storage spool.

During the drawing process, applying the thermoplastic polymer coating layer 234 before the light diffusing optical fiber 210 reaches the fiber collection unit prevent mechanical contact between the cladding 222 and the one or more drawing mechanisms of the fiber collection unit, which may prevent damage to the glass of the cladding 222. However, in other embodiments, the thermoplastic polymer coating layer 234 is applied to the light diffusing optical fiber 210 after the light diffusing optical fiber 210 is drawn, for example, using off-draw equipment, such as conventional extruding equipment. Thus, in embodiments in which the thermoplastic polymer coating layer 234 is applied after a draw process, it may be desirable to apply a coating layer onto the cladding 222 during the draw process to prevent damage to the glass of the cladding 122 caused by the drawing mechanisms and tensioning pulleys of the fiber collection unit. An example light diffusing optical fiber having a polymer layer between a cladding and a thermoplastic polymer coating layer is the light diffusing optical fiber 310, described below.

Referring now to FIGS. 4A and 4B, cross sections the light diffusing optical fiber 310 comprising the core 320, the cladding 322 surrounding the core 320, scattering structures 325, a primary coating layer 330 surrounding the cladding 322, and a thermoplastic polymer coating layer 334 surrounding the primary coating layer 330 such that the primary coating layer 330 is disposed between the cladding 322 and the thermoplastic polymer coating layer 334 are depicted. The core 320 comprises a glass core (e.g., silica) doped with a hydroxyl material (e.g., silica comprising about 300 ppm or more of a hydroxyl material). The cladding 322 comprises a glass cladding (e.g., F-doped silica or F (fluorine)/B (boron) co-doped silica having a lower refractive index than the refractive index of the core 320) doped with a hydroxyl material (e.g., doped silica or F (fluorine)/B (boron) co-doped silica comprising about 300 ppm or more of a hydroxyl material). The scattering structures 325 may occur throughout the core 320 (as depicted in FIGS. 4A and 4B), or may occur near the interface of the core 320 and the cladding 322 (e.g., the core-cladding boundary), or may occur in an annular ring within the core 320. The scattering structures 325 may comprise any of the scattering structures 125 described above with respect to the light diffusing optical fiber 110, for example, gas filled voids, scattering particles, such as ceramic materials, dopants, or the like.

The thermoplastic polymer coating layer 334 may comprise any of the fluorinated polymer materials of the thermoplastic polymer coating layer 234, such as polytetrafluoroethylene (PTFE), such as Teflon™, ethylene-tetrafluoroethylene (ETFE), such as Tefzel™, polyethylene terephthalate (PET), fluorinated ethylene propylene (FEP), perfluoroalkoxy alkane (PFA), PEEK (polyetheretherketone), Nylon, and any other fluorinated extrudable polymer. The thermoplastic polymer coating layer 334 comprises low absorbance of UV light and visible, blue-violet light and is a hard plastic material, which provides a protective coating layer surrounding the core 320, the cladding 322, and the primary coating layer 330.

The primary coating layer 330 comprises a UV curable coating layer, such as cycloaliphatic epoxy. While cycloaliphatic epoxy is UV curable, the photo-initiator used to cure the cycloaliphatic epoxy is UV absorptive but is removable after the cycloaliphatic epoxy is cured, for example, by bleaching the cycloaliphatic epoxy, and the resultant cured cycloaliphatic epoxy comprises low absorbance of UV light and visible, blue-violet light as described in more detail below with respect to graph 50 of FIG. 5, below. In some embodiments, the photo-initiator comprises (p-isopropylphenyl)(p-methylphenyl)iodonium tetrakis(pentafluorophenyl)borate. Further, the primary coating layer 330 may comprise a thickness of from about 5 μm to about 20 μm, for example, from about 10 μm to about 15 μm. It may be advantageous for the primary coating layer 330 to be thin because some UV light and visible, blue-violet light may still be absorbed by the primary coating layer 330 and a thinner layer minimizes this absorption.

Referring still to FIGS. 4A and 4B, the primary coating layer 330 is doped with a plurality of scattering particles 335, which may comprise any of the scattering particles 135 described above with respect to the light diffusing optical fiber 110. For example, the scattering particles 335 may comprise low absorption scattering materials having a refractive index greater than the cycloaliphatic epoxy of the primary coating layer 330 (which comprises a refractive index of about 1.41), for example, $Al_2O_3$ having a refractive index of about 1.77, $BaSO_4$ having a refractive index of about 1.636, particles made from thermoplastic polymer such as polytetrafluoroethylene (PTFE), such as Teflon™, ethylene-tetrafluoroethylene (ETFE), such as Tefzel™, polyethylene terephthalate (PET), fluorinated ethylene propylene (FEP), perfluoroalkoxy alkane (PFA), PEEK (polyetheretherketone), Nylon, and any other fluorinated polymer, or the like. Further, in some embodiments, the scattering particles 335 may instead or in addition comprise gas voids or microbubbles. Moreover, while FIGS. 4A and 4B depict that the plurality of scattering particles 335 are disposed in the primary coating layer 330, the plurality of scattering particles 335 may alternatively or additionally be disposed in the thermoplastic polymer coating layer 334.

Referring again to FIGS. 1, 2B, 3B, and 4B, in operation, unscattered, guided light (such as UV light or visible, blue-violet light output by the light source 152 of the light output device 102) propagates along the light diffusing optical fiber 110, 210, 310 in the direction shown by arrow 10. Scattered light is shown exiting the light diffusing optical fiber 110, 210, 310 in the direction shown by arrow 12 at a scattering angle $\theta_s$, which is the angular difference between the propagation direction 10 of guided light propagating along the light diffusing optical fiber 110, 210, 310 and the direction 12 of the scattered light when it leaves light diffusing optical fiber 110. In some embodiments, the intensities of the spectra when the scattering angle $\theta_s$ is between 15° and 150°, or 30° and 130° are within ±50%, ±30%, ±25%, ±20%, ±15%, ±10%, or ±5% as measured at the peak wavelength. In some embodiments, the intensities of the spectra when the scattering angle $\theta_s$ is between all angles within 30° and 130°, or 40° and 120° are at least within ±50%, for example ±30%, ±25%, ±20%, ±15%, ±10%, or ±5% as measured at the peak wavelength. Accordingly, each light diffusing optical fiber 110, 210, 310 is configured to provide substantially uniform illumination due to scattering, such that the difference between the minimum and maximum scattering illumination intensity is less than 50% of the maximum scattering illumination intensity, for all viewing angles between at least 40 degrees and 110 degrees, for example for all viewing angles between 40 degrees and 120 degrees. According to some embodiments, the difference between the minimum and maximum scattering illumination intensity is not greater than 30% of the maximum scattering illumination intensity.

Referring again to FIGS. 2A-4B, each light diffusing optical fiber 110, 210, 310 may have a scattering induced attenuation loss of greater than about 0.2 dB/m at a wavelength of 550 nm. For example, in some embodiments, the scattering induced attenuation loss (attenuation loss due to the scattering structures 125, 225, 325, such as air lines) may be greater than about 0.5 dB/m, 0.6 dB/m, 0.7 dB/m, 0.8 dB/m, 0.9 dB/m, 1 dB/m, 1.2 dB/m, 1.4 dB/m, 1.6 dB/m, 1.8 dB/m, 2.0 dB/m, 2.5 dB/m, 3.0 dB/m, 3.5 dB/m, or 4 dB/m, 5 dB/m, 6 dB/m, 7 dB/m, 8 dB/m, 9 dB/m, 10 dB/m, 20 dB/m, 30 dB/m, 40 dB/m, or 50 dB/m at 550 nm. In some embodiments, the average scattering loss of the light diffusing optical fiber 110, 210, 310 is greater than 50 dB/km, and the scattering loss does not vary more than 20% (i.e., the scattering loss is within ±20% of the average scattering loss, for example within ±15%, or within ±10%) over any given fiber segment of the light diffusing optical fiber 110. In some embodiments, the average scattering loss of the light diffusing optical fiber 110, 210, 310 is greater than 50 dB/km, and the scattering loss does not vary more than 20% (i.e., the scattering loss is within ±20% of the average scattering loss, for example within ±15%, or even within ±10%) over any given fiber segment of the light diffusing optical fiber 110, 210, 310 of from about 0.2 m to about 50 m, for example, 0.5 m, 1 m, 2 m, 5 m, 10 m, 15 m, 20 m, 25 m, 30 m, 35 m, 40 m, 45 m, or the like.

Figure 5:
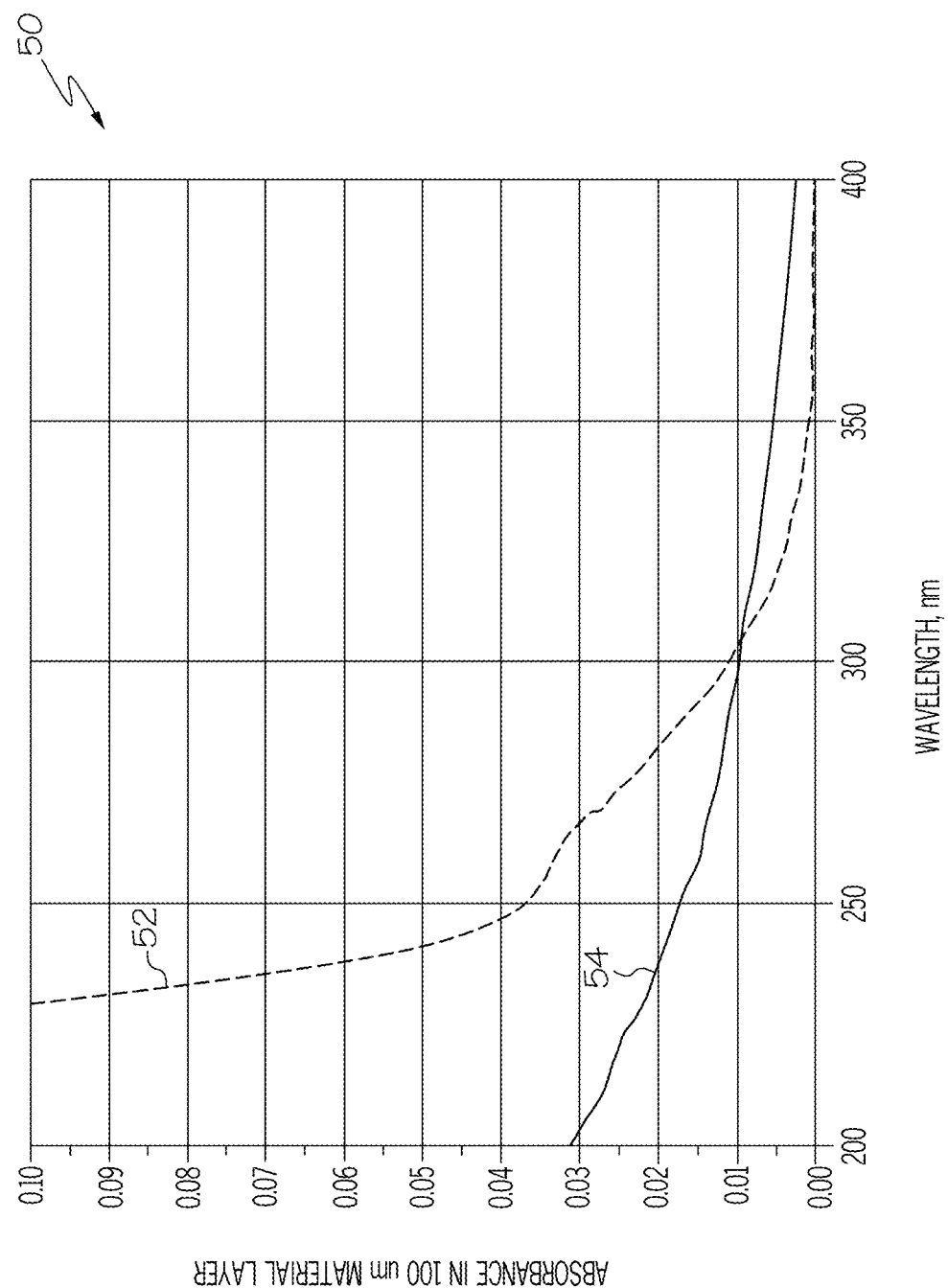
FIG. 5 graphically depicts the absorbance of ultraviolet light for various polymer materials, according to one or more embodiments shown and described herein.

Referring now to FIG. 5, a graph 50 depicts the absorbance of UV light from 200 nm to 400 nm in sample material layers comprising a thickness of about 100 μm. One sample material layer is a cycloaliphatic epoxy comprising a thickness of about 100 μm, such as the cycloaliphatic epoxy of the primary coating layer 330 of the light diffusing optical fiber 310, which is represented by line 52. Another sample material layer comprising a thickness of about 100 μm is PTFE, such as the thermoplastic polymer coating layer 234 of light diffusing optical fiber 210 and the thermoplastic polymer coating layer 334 of the light diffusing optical fiber 310, which is represented by line 54. As depicted by line 52, the cycloaliphatic epoxy comprises an absorbance per 100 μm of thickness of about 0.0005 at 400 nm, about 0.001 at 375 nm, about 0.002 at 350 nm, about 0.004 at 325 nm, about 0.012 at 300 nm, about 0.025 at 275 nm, and about 0.035 at 250 nm. Further, as depicted by line 54, the PTFE comprises an absorbance per 100 μm of thickness of about 0.003 at 400 nm, about 0.004 at 375 nm, about 0.006 at 350 nm, about 0.008 at 325 nm, about 0.01 at 300 nm, about 0.013 at 275 nm, about 0.0175 at 250 nm, about 0.024 at 225 nm, and about 0.032 at 200 nm.

Referring still to FIG. 5, the cycloaliphatic epoxy (line 52) comprises an absorbance per 100 μm of thickness of about 0.01 or less for light comprising a wavelength of about 310 nm or more. The cycloaliphatic epoxy (line 52) comprises an absorbance per 100 μm of thickness of about 0.02 or less for light comprising a wavelength of about 250 nm or more. The cycloaliphatic epoxy (line 52) comprises an absorbance per 100 μm of thickness of about 0.03 or less for light comprising a wavelength of about 270 nm or more. Further, the cycloaliphatic epoxy (line 52) comprises an absorbance per 100 μm of thickness of about 0.04 or less for light comprising a wavelength of about 245 nm or more. The PTFE (line 54) comprises an absorbance per 100 μm of thickness of about 0.01 or less for light comprising a wavelength of about 300 nm or more. The PTFE (line 54) comprises an absorbance per 100 μm of thickness of about 0.02 or less for light comprising a wavelength of about 240 nm or more. Further, the PTFE (line 54) comprises an absorbance per 100 μm of thickness of about 0.03 or less for light comprising a wavelength of about 205 nm or more.

Figure 6:
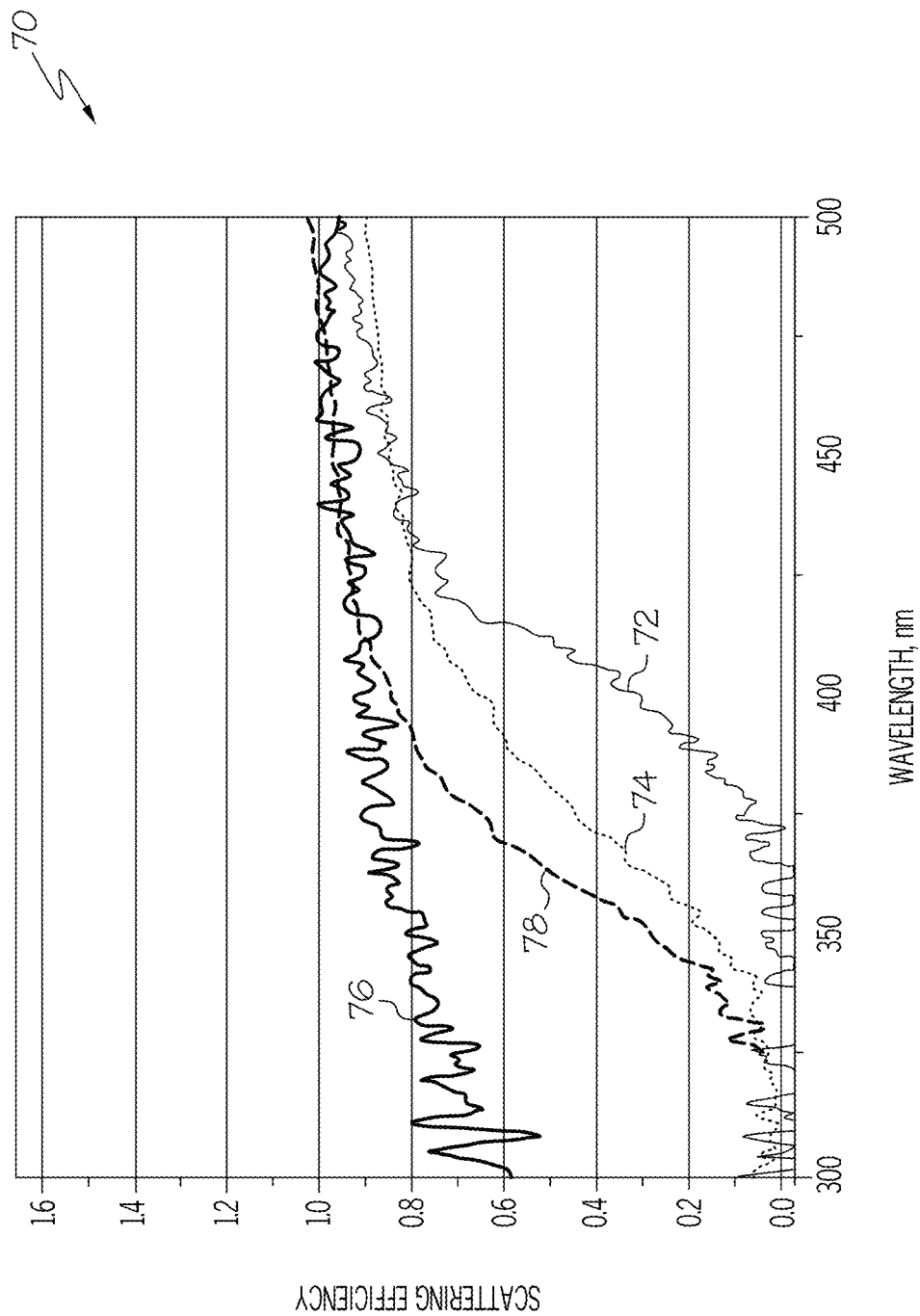
FIG. 6 graphically depicts the scattering efficiency of ultraviolet light for various embodiments of light diffusing optical fibers, according to one or more embodiments shown and described herein.

Referring now to FIG. 6, graph 70 depicts the scattering efficiency of various light diffusing optical fiber embodiments for light comprising a wavelength of from about 300 nm to about 500 nm. As stated previously, "scattering efficiency" refers to the percentage of light scattering outward from the core 120, 220, 320 of the light diffusing optical fiber 110, 210, 310 towards the outer surface 128, 228, 328 that in not absorbed, blocked, or otherwise lost, and in fact exits the outer surface 128, 228, 328. In FIG. 6, line 72 represents a previous embodiment of a light diffusing optical fiber, line 74 represents the light diffusing optical fiber 110, line 76 represents the light diffusing optical fiber 210, and line 78 represents the light diffusing optical fiber 310. As depicted in FIG. 6, the light diffusing optical fibers 110, 210, 310 described herein comprise higher scattering efficiencies of UV light than previous light diffusing optical fibers.

Referring still to FIG. 6, line 74 depicts that the light diffusing optical fiber 110 comprises a scattering efficiency of about 0.1 or more for light comprising a wavelength of about 350 nm or more, a scattering efficiency of about 0.4 or more for light comprising a wavelength of about 375 nm or more, a scattering efficiency of about 0.6 or more for light comprising a wavelength of about 400 nm or more, and a scattering efficiency of about 0.8 or more for light comprising a wavelength of about 425 nm or more. Line 76 depicts that the light diffusing optical fiber 210 comprises a scattering efficiency of about 0.5 or more for light comprising a wavelength of about 300 nm or more, a scattering efficiency of about 0.65 or more for light comprising a wavelength of about 325 nm or more, a scattering efficiency of about 0.75 or more for light comprising a wavelength of about 350 nm or more, a scattering efficiency of about 0.8 or more for light comprising a wavelength of about 375 nm or more, and a scattering efficiency of about 0.9 or more for light comprising a wavelength of about 400 nm or more. Further, while not depicted in FIG. 6, light diffusing optical fiber 210 comprises a scattering efficiency of about 0.4 or more for light comprising a wavelength of about 250 nm or more, such as a scattering efficiency of about 0.5 or more. Moreover, line 78 depicts that the light diffusing optical fiber 310 comprises a scattering efficiency of about 0.3 or more for light comprising a wavelength of about 350 nm or more, a scattering efficiency of about 0.6 or more for light comprising a wavelength of about 375 nm or more, a scattering efficiency of about 0.8 or more for light comprising a wavelength of about 400 nm or more, and a scattering efficiency of about 0.9 or more for light comprising a wavelength of about 425 nm or more.

One aspect of this disclosure pertains to a light delivery system for delivering blue-violet light that includes a blue-violet light irradiating device that emits a light comprising an average power density of about 5 mW/cm$^2$ to about 30 mW/cm$^2$ at a wavelength from about 380 nm to about 495 nm, wherein after a pathogen sample comprising an amount of colony forming units is irradiated with the light for an exposure time from about 30 minutes to about 48 hours (e.g., from about 2 hours to about 8 hours, or from about 4 hours to about 24 hours), the amount of colony forming units of the pathogen sample are reduced by about a 4-Log reduction to about a 9-Log reduction.

In one or more embodiments, the light delivery system comprises one or more light diffusing optical fibers. In one or more embodiments, the light emitted by the system has an average power density from about 7.2 mW/cm$^2$ to about 11.25 mW/cm$^2$. The light may be pulsed or constant, as otherwise described herein.

The light delivery system may include a light source optically connected to the light irradiating device, wherein the light source is linearly polarized. In one or more embodiments, the system may include a light source that is optically connected to the light irradiating device, wherein the light source is a laser diode.

In one or more embodiments, the light delivery system is used for disinfection and includes a light irradiating device for irradiating a pathogen with a light in vivo, ex vivo or both in vivo and ex vivo, wherein the pathogen comprising an amount of colony forming units, wherein the light comprising an average power density of about 5 mW/cm$^2$ to about 30 mW/cm$^2$ at a wavelength from about 380 nm to about 495 nm, and wherein when the pathogen is irradiated with the light for an exposure time from about 30 minutes to about 48 hours, the amount of colony forming units of the pathogen sample are reduced by about a 4-Log reduction to about a 9-Log reduction. In one or more embodiments, the light irradiating device is positioned at a distance of about 30 mm or less from the pathogen. In one or more embodiments, the light irradiating device is positioned at a distance from about 2 mm to about 30 mm or less from the pathogen. In one or more embodiments, the light irradiating device is in contact with the pathogen. In one or more embodiments, the light irradiating device is positioned at a distance from about 2 mm to about 30 mm or less from the pathogen. The light may be pulsed or constant, as otherwise described herein.

In one or embodiments, the light delivery systems described herein may be used to irradiate a pathogen that is a gram-positive pathogen (e.g., one of *Staphylococcus aureus, Staphylococcus epidermidis, Candida albicans, Streptococcus pyogenes,* and *Enterococcus faecium*). In one or more embodiments, the light delivery systems described herein may be used to irradiate a pathogen that is a gram-negative pathogen (e.g., at least one of *Pseudomonas aeruginosa, Escherichia coli, Acinetobacter baumannii, Klebsiella pneumoniae,* and *Enterobacter aerogenes*). In one or more embodiments, wherein, when the pathogen is *Enterococcus faecium,* and after pathogen is irradiated with the light having an average power density 25 mW/cm$^2$ for an exposure time of about 6 hours, the amount of colony forming units of the pathogen sample are reduced by about a 4-Log reduction or greater. In one or more embodiments, wherein, when the pathogen is *Staphylococcus aureus,* and after pathogen is irradiated with the light having an average power density 10 mW/cm$^2$ for an exposure time of about 4 hours or with the light having a power density of 25 mW/cm$^2$ for an exposure time of about 2 hours, the amount of colony forming units of the pathogen sample are reduced by about a 4-Log reduction or greater. In one or more embodiments, wherein, when the pathogen is *Klebsiella pneumoniae,* and after pathogen is irradiated with the light having an average power density 10 mW/cm$^2$ for an exposure time of about 6 hours, the amount of colony forming units of the pathogen sample are reduced by about a 4-Log reduction or greater.

In one or more embodiments, wherein, when the pathogen is *Acinetobacter baumannii,* and after pathogen is irradiated with the light having an average power density 10 mW/cm$^2$ for an exposure time of about 4 hours or with the light having a power density of 25 mW/cm$^2$ for an exposure time of about 2 hours, the amount of colony forming units of the pathogen sample are reduced by about a 4-Log reduction or greater.

In one or more embodiments, wherein, when the pathogen is *Pseudomonas aeruginosa,* and after pathogen is irradiated with the light having an average power density 10 mW/cm$^2$ for an exposure time of about 2, the amount of colony forming units of the pathogen sample are reduced by about a 4-Log reduction or greater.

In one or more embodiments, wherein, when the pathogen is *Streptococcus pyogenes,* and after pathogen is irradiated with the light having an average power density 5 mW/cm$^2$ for an exposure time of about 2, the amount of colony forming units of the pathogen sample are reduced by about a 4-Log reduction or greater.

In one or more embodiments, wherein, when the pathogen is *Candida albicans,* and after pathogen is irradiated with the light having an average power density 10 mW/cm$^2$ for an exposure time of about 6 or with the light having a power density of 25 mW/cm$^2$ for an exposure time of about 4 hours, the amount of colony forming units of the pathogen sample are reduced by about a 4-Log reduction or greater.

In one or more embodiments, wherein, when the pathogen is *Escherichia coli,* and after pathogen is irradiated with the light having an average power density 10 mW/cm$^2$ for an exposure time of about 6 or with the light having a power density of 25 mW/cm$^2$ for an exposure time of about 4 hours, the amount of colony forming units of the pathogen sample are reduced by about a 4-Log reduction or greater.

Embodiments of a light diffusing optical fiber that can be incorporated into the light delivery systems have been described herein; however, the systems should not be limited to such fibers. Referring now to FIGS. 7-9B, methods of using a blue-violet light delivery system as a light delivery tool for disinfecting will now be described. It has been discovered that by optically engaging pathogens with visible, blue-violet light from the systems described herein, an antimicrobial and/or disinfecting result can be achieved. In general and while not intending to be limited by theory, visible, blue-violet light causes increases in cell reactive oxygen species production in pathogen cells leading to cell death. Unlike the use of UV light (e.g. UVA, UVB or UVC), the use of visible, blue-violet light reduces negative effects to mammalian DNA mutations and cell death. As discussed in more detail herein, to achieve pathogen cell death and bactericidal effects the visible, blue-violet light radiating from the blue-violet light delivery system described herein, the light irradiated must be delivered using prescribed power densities, wavelengths, and exposure times.

Figure 7:
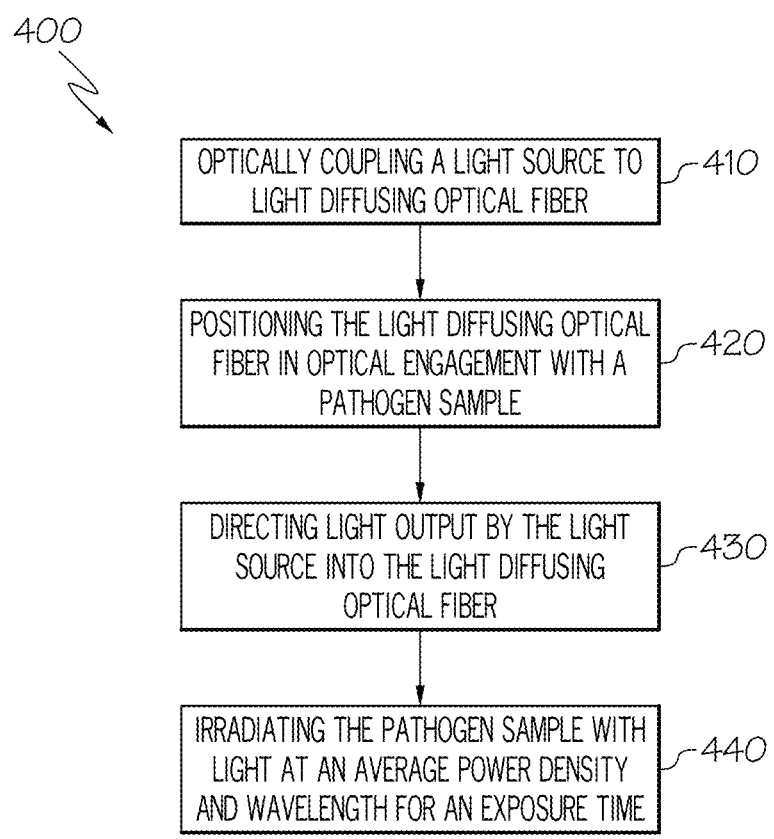
FIG. 7 is a flowchart depicting a method of disinfecting using light diffusing optical fiber according to one or more embodiments shown and described herein.

Referring now to FIG. 7, an example method of disinfecting using a blue-violet light delivery system is depicted flowchart 400. In step 410, the light source 152 from the light output device 102 is coupled to the blue-violet light delivery system (or one or more light diffusing optical fibers, if applicable). The light output device 102 may further comprise additional optical components such as a lens, an optical delivery fiber, or the like, positioned between and optically coupled to the light source 152 and the first end 112 of the blue-violet light delivery system (or light diffusing optical fiber 110) to facilitate the input of light into the blue-violet light delivery system (or light diffusing optical fiber 110). Moreover, these additional optical components, such as an optical delivery fiber, may allow the light source 152 to be spatially separated from the blue-violet light delivery system (or light diffusing optical fiber 110).

As discussed in more detail above, the light diffusing optical fiber comprises a core, cladding, an outer surface and a plurality of scattering structures positioned in the core, the cladding, or both the core and the cladding. In operation, the scattering structures of the one or more light diffusing optical fibers scatter light propagating along the one or more light diffusing optical fibers toward the outer surface and a portion of the light diffuses through the outer surface.

In step 420, the blue-violet light delivery system (or one or more light diffusing optical fibers) are positioned in optical engagement with a pathogen sample. As used herein, "optical engagement" refers to an arrangement where the one or more light diffusing optical fibers may directly or indirectly illuminate a pathogen sample with light. In one or more embodiments, the light diffuses through the outer surface of the one or more light diffusing optical fibers. It is advantageous to minimize the spacing between the blue-violet light delivery system (or the one or more light diffusing optical fibers) and the pathogen sample to achieve a high efficacy of energy that is output by the blue-violet light delivery system (one or more light diffusing optical fibers) and absorbed by the pathogen sample. As used herein with respect to the term "optical engagement," "directly" may refer to contact with the pathogen sample or separated by an air gap between the blue-violet light delivery system (or one or more light diffusing optical fibers) and the pathogen sample and "indirectly" may refer to a material positioned between the blue-violet light delivery system (or one or more light diffusing optical fibers) and the pathogen sample that generally does not impede the average power, wavelength or exposure time of the light delivered from the blue-violet light delivery system (or one or more light diffusing optical fibers) to the pathogen sample, such as a visible, blue-violet light transmission material. In some embodiments, the blue-violet light delivery system (one or more light diffusing optical fibers) may be in direct contact with the pathogen sample.

In step 430, light output by the light source is directed into the one or more light diffusing optical fibers for a first time interval. In response to step 430, light diffuses through the outer surface of the one or more light diffusing optical fibers thereby irradiating the pathogen sample with light having an average power density at a wavelength for an exposure time. In some embodiments, the light delivered to the pathogen sample has an average power density from about 5 mW/cm$^2$ to about 30 mW/cm$^2$, or from about 7.2 mW/cm$^2$ to about 11.25 mW/cm$^2$. For example, in some embodiments, the average power density is about 5 mW/cm$^2$, 6 mW/cm$^2$, 7 mW/cm$^2$, 8 mW/cm$^2$, 9 mW/cm$^2$, 10 mW/cm$^2$, 11 mW/cm$^2$, 12 mW/cm$^2$, 13 mW/cm$^2$, 14 mW/cm$^2$, 15 mW/cm$^2$, 16 mW/cm$^2$, 17 mW/cm$^2$, 18 mW/cm$^2$, 19 mW/cm$^2$, 20 mW/cm$^2$, 21 mW/cm$^2$, 22 mW/cm$^2$, 23 mW/cm$^2$, 24 mW/cm$^2$, 25 mW/cm$^2$, 26 mW/cm$^2$, 27 mW/cm$^2$, 28 mW/cm$^2$, 29 mW/cm$^2$, or 30 mW/cm$^2$. Moreover, the light delivered to the pathogen sample has a wavelength from about 380 nm to about 495 nm, i.e., a UV-blue-violet boarder range, or from about 400 nm to about 410 nm, or 405 nm. For example, in some embodiments, the wavelength is from about 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, or the like.

Additionally, as used herein, "exposure time" refers to the time intervals in which the pathogen sample is irradiated by the light delivered from the blue-violet light delivery system (or one or more light diffusing optical fibers). In some embodiments, the exposure time may be from about 30 minutes to about 48 hours, or from about 2 hours to about 48 hours, or from about 30 minutes to about 24 hours, or from about 2 to about 24 hours, or from about 2 to about 8 hours, or from 4 hours to about 24 hours. For example, in some embodiments, the exposure time is about 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours or more. That is, exposure time may be continuous, i.e., greater than 30 minutes, greater than 6 hours, greater than 24 hours, or greater than 48 hours.

In some embodiments, the light delivered from the blue-violet light delivery system (or one or more light diffusing optical fibers) at an average power density for an exposure time yields in an energy density ranging, for example, from about 36 J/cm$^2$ to about 972 J/cm$^2$ being delivered to the pathogen sample. In some embodiments, the total energy density is from about 103 J/cm$^2$ to about 972 J/cm$^2$. In general, the total energy density delivered to the pathogen sample from the light diffused from the blue-violet light delivery system (or one or more light diffusing optical fibers) is a function of power density and the exposure time, i.e., average power density times exposure time is total energy density (e.g. ~7.2 mW/cm$^2$*3600 s/hr*1 J/1000 mJ*6 hr=~155.52 J/cm$^2$. For example, when ~1×10$^4$ CFUs (colony forming units) of a pathogen are exposed to light yielding an energy density of ~155 J/cm$^2$, the effect is bactericidal (i.e. pathogen cell death) leading to about a 4-Log to 9-Log reduction in CFUs, e.g., from about 10,000 times fewer to about 1,000,000,000 times fewer CFUs.

In some embodiments, the light may be provided in a continuous fashion at a continuous power density. In other embodiments, the light may be provided in a continuous fashion with a varying power density. In other embodiments, the light may be provided in a pulsed fashion at varying power densities to achieve an overall average power density during a time interval. In yet other embodiments, the light may be provided in a pulsed fashion where the power density of light for each pulse is the same.

Figure 8A:
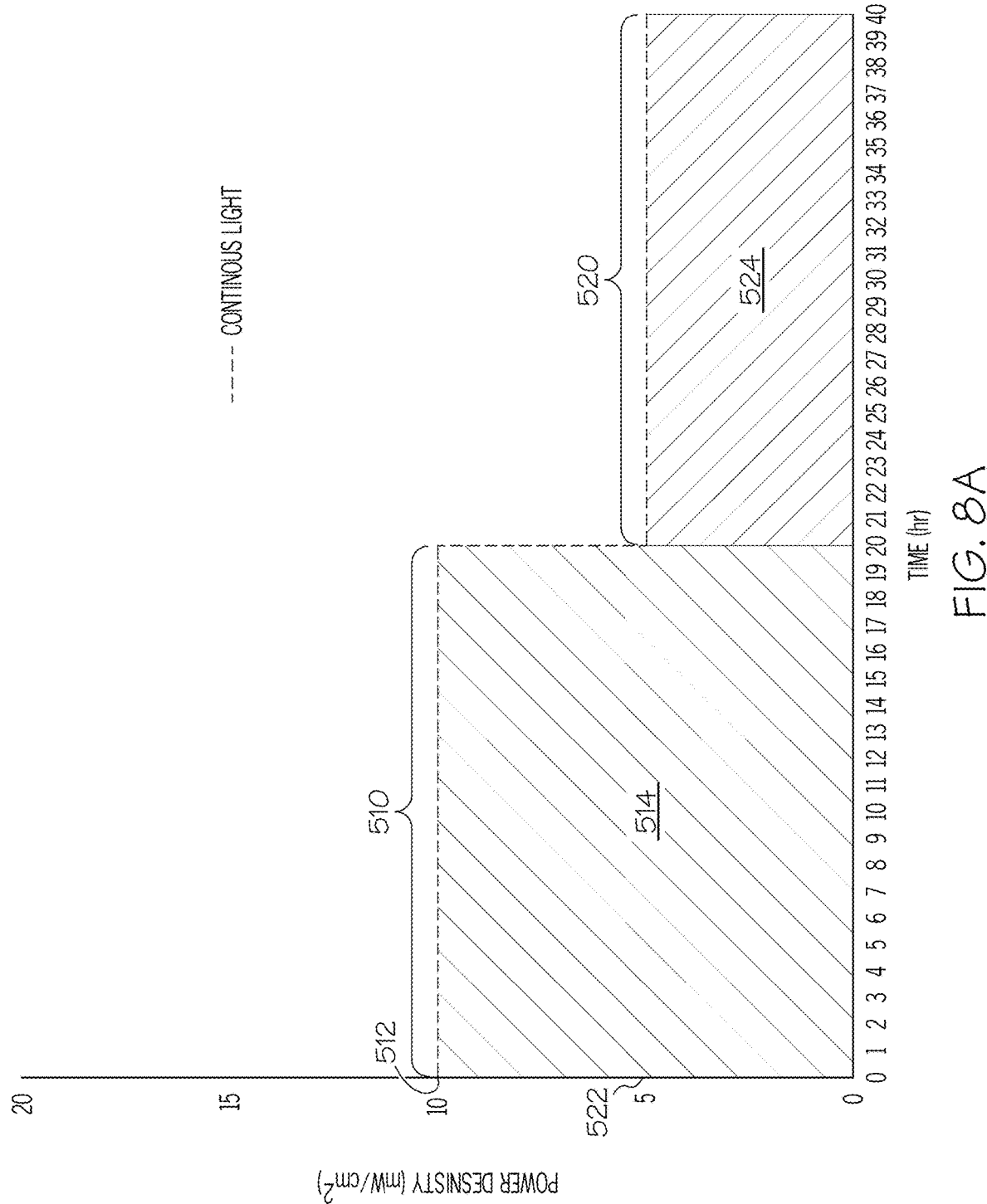
FIG. 8A graphically depicts light output by the light diffusing optical fiber over two time intervals according to one or more embodiments shown and described herein.
Figure 8B:
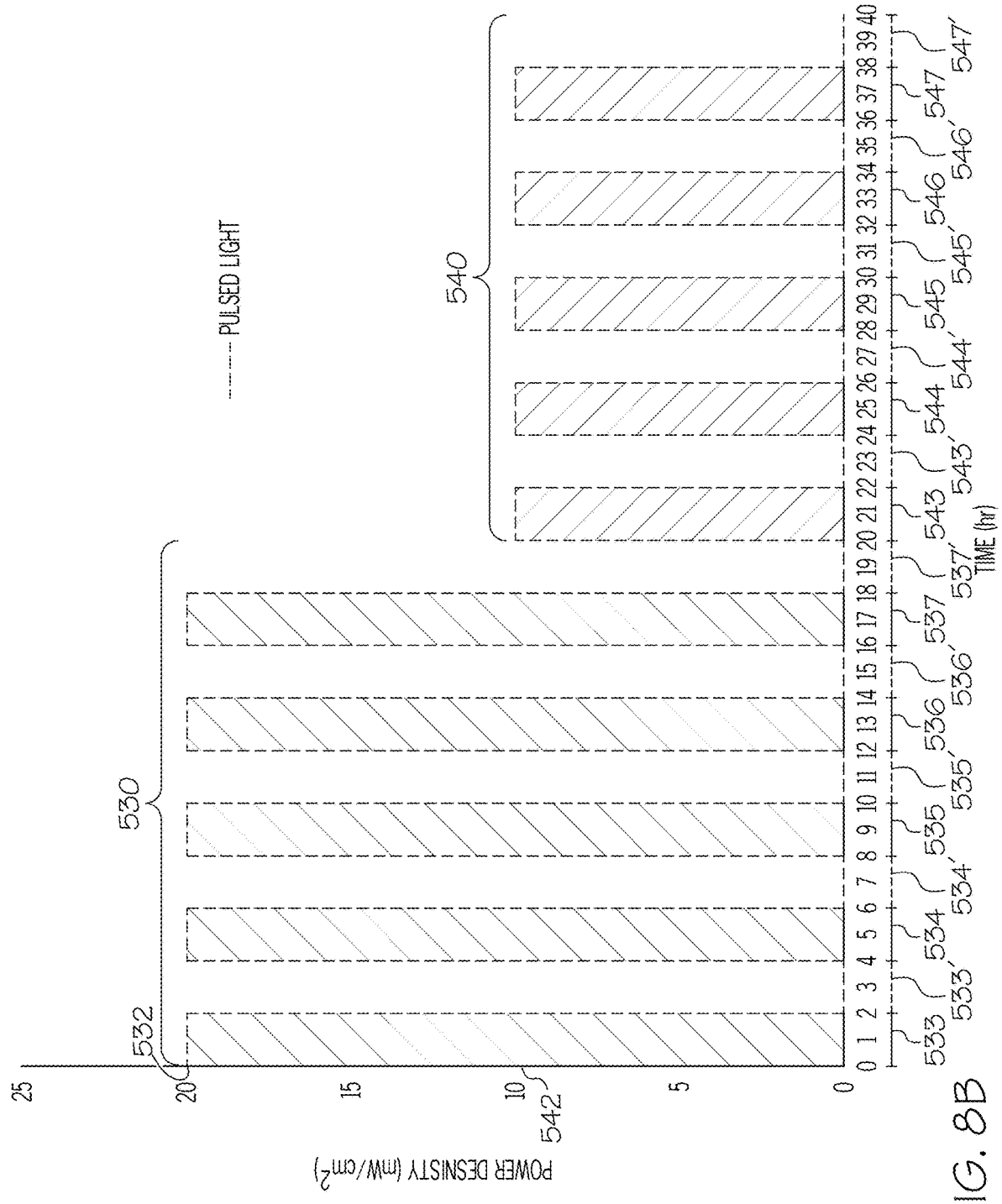
FIG. 8B graphically depicts light output by the light diffusing optical fiber over two time intervals according to one or more embodiments shown and described herein.

Referring now to FIGS. 8A-8B, two examples of light delivery are graphically depicted as a function of power density over two time intervals. For example, referring to FIG. 8A, light is delivered for a first time interval 510 at a power density level 512 of 10 mW/cm$^2$ for an exposure time totaling 20 hrs, yielding a total energy density 514 of 720 J/cm$^2$. Light is subsequently delivered for a second time interval 520 at a power density level 522 of 5 mW/cm$^2$ for an exposure time totaling 20 hrs, yielding a total energy density 524 of 360 J/cm$^2$. In some embodiments, light is delivered during a first time interval and not a second time interval. However, in some applications it is advantageous to have two or more time intervals of varying power densities and exposure times. Such configurations may provide for treatment of large amounts of CFUs and subsequent maintenance intervals to prevent small amount of CFUs from repopulating.

In another embodiment, referring to FIG. 8B, light is delivered in a pulsed configuration. For example, light is delivered for a first time interval 530 at a power density 532 of 20 mW/cm$^2$ for a total exposure time of 10 hours over a the first time interval 530 of 20 hours. That is, the light source directs light into the blue-violet light delivery system (or one or more light diffusing fibers) in alternating 2 hours intervals resulting in a pulsed pattern of light being output to the pathogen sample. For example, during exposure time 533 of 2 hours the power density is 20 mW/cm$^2$ followed by an off period of time 533' of 2 hours resulting in first 4 hours of the first time interval 530 of 20 hours. The pulsed pattern of light for the first time interval 530 repeats where during exposure times 533, 534, 535, 536 and 537 the light is output from the blue-violet light delivery system (or one or more light diffusing optical fibers) to the pathogen sample each have a power density 532 of 20 mW/cm$^2$ and during the off period of times 533', 534', 535', 536' and 537' no light is output from the blue-violet light delivery system (or one or more light diffusing optical fibers) to the pathogen sample. The resulting average power density 532 during the first time interval is therefore 10 mW/cm$^2$. Furthermore, the resulting total energy density is a function of the power density during each exposure time 533, 534, 535, 536 and 537, for example yielding about 720 J/cm$^2$ during the first time interval depicted in FIG. 8B.

FIG. 8B further depicts a second time interval 540 where the light is delivered in a pulsed configuration with a power density 542 of 10 mW/cm$^2$ during each exposure time 543, 544, 545, 546, and 547 and where no light is delivered during each off period of time 543', 544', 545', 546' and 547'. The resulting average power density 542 during the first time interval is therefore 5 mW/cm$^2$. Furthermore, the resulting total energy density is a function of the power density during each exposure time 543, 544, 545, 546 and 547, for example yielding about 360 J/cm$^2$ during the second time interval depicted in FIG. 8B.

In some embodiments, for example, the light source may be configured to output pulsed light in a first pulse cycle (e.g., a first time interval 530) and a second pulse cycle (e.g., a second time interval 540). The first pulse cycle may output one or more pulses (e.g., as by the exposure times 533, 534, 535, 536 and 537) where the total of the exposure times 533, 534, 535, 536 and 537 is a first pulse duration. The second pulse cycle may output one or more pulses (e.g., as shown by the exposure times 543, 544, 545, 546 and 547) where the total of the exposure times 543, 544, 545, 546 and 547 is a second pulse duration.

Pulsing the light delivered to the pathogen sample with intervals of higher power densities than a constant application of light may be advantageous for disinfecting large amounts of CFUs, and/or improving the efficiency of the disinfection process, and/or combating aggressive or robust forms of pathogens. Additionally, by adjusting the power density and the exposure time, the total energy density delivered to the pathogen sample may be adjusted.

In some embodiments, the exposure time for each pulse of light in a time interval may be greater than the off period of time. In other embodiments, the exposure time for each pulse of light is less than the off period of time. Similarly, while the term "off period of time" is used herein with reference to a period of time where no light is output to the pathogen sample, one skilled in the art may configure the pulsed light output by the blue-violet light delivery system (or one or more light diffusing optical fibers) to have a first power density during a first exposure time followed by a second power density during a second exposure time that is different than the first power density. Furthermore, both the first power density and the second power density may be greater than 0 mW/cm$^2$.

Figure 9A:
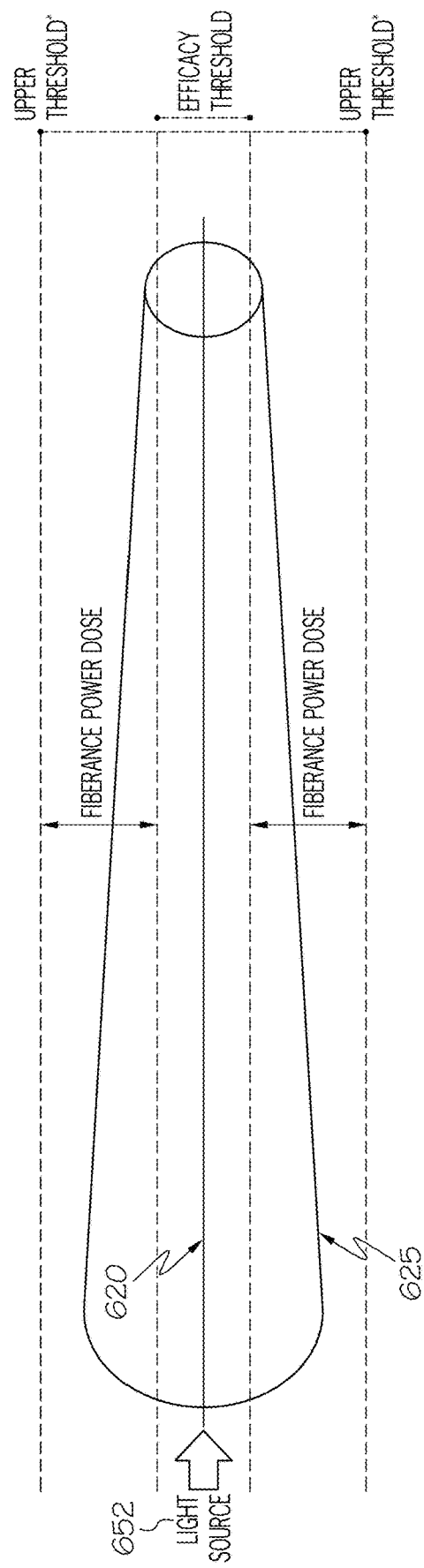
FIG. 9A schematically depicts a cylindrical tube dispersing light along the light diffusing optical fiber according to one or more embodiments shown and described herein.

As described below with respect to the experimental configurations, some embodiments may include light diffusing optical fiber configurations where one or more light diffusing optical fibers are configured in a structured configuration. Without intending to be limited by theory, referring to FIGS. 9A-9B, as light 652 propagates through the light diffusing optical fiber 620 light diffuses but drops off along the length of the fiber as shown by numeral 625. FIG. 9A shows an example decay of energy of the diffused light along the light diffusing optical fiber. In order to be effective for disinfecting purposes, the energy of the diffused light should be above an efficacy threshold. In some embodiments it is contemplated that an upper threshold should be configured to also assure effective disinfection without adverse effects.

Figure 9B:
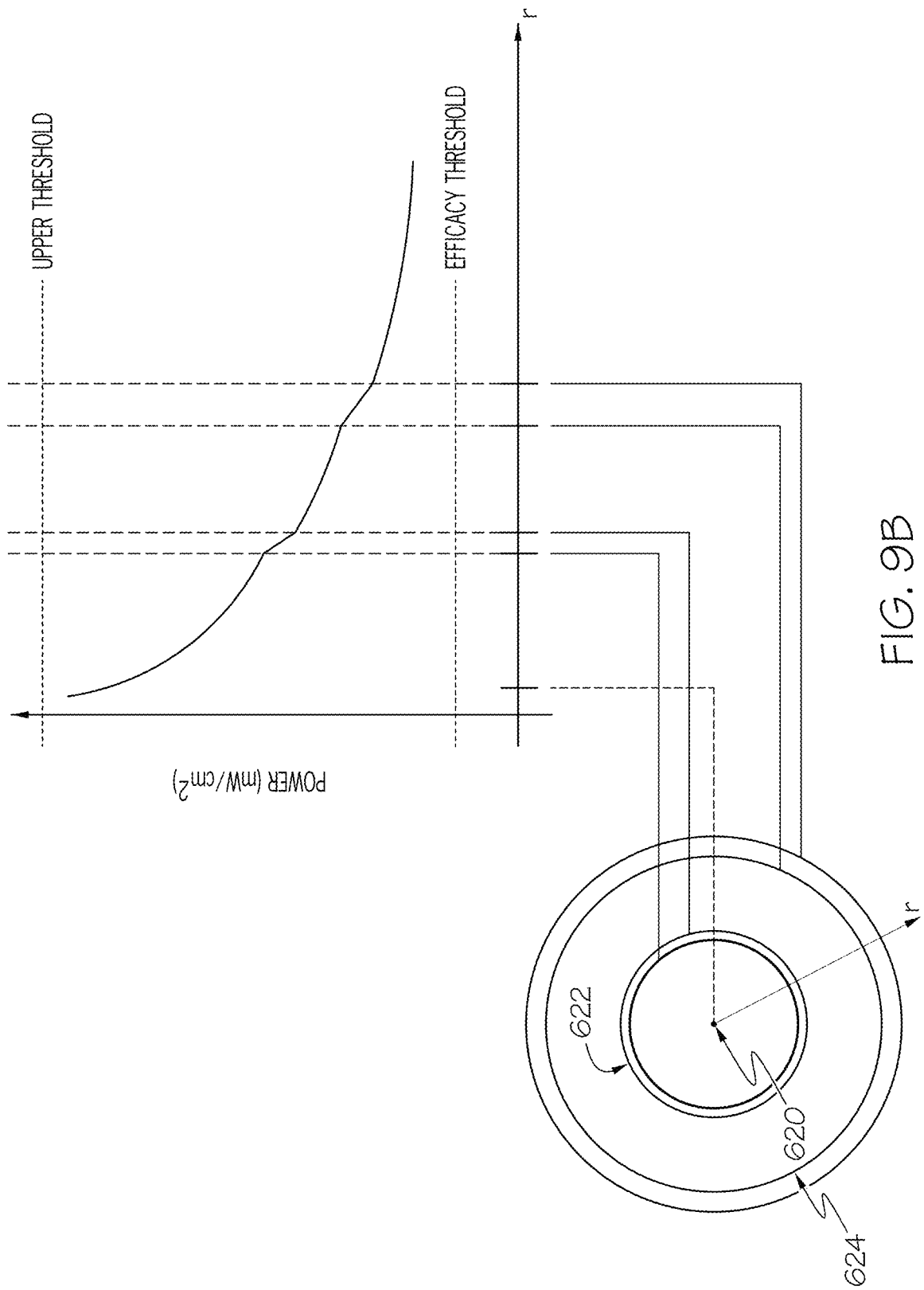
FIG. 9B schematically and graphically depicts the effect of power absorbance when passing through multiple cylindrical tubes as show in the cross-section according to one or more embodiments shown and described herein.

In further embodiments, the light diffusing optical fiber may be encased or positioned within one or more cylindrical tubes 622 and 624. As shown in FIG. 9B, each layer of tube 622 and 624 results in an absorbance of energy of the diffused light. Therefore, in order for the diffused light to remain effective for disinfecting purposes the initial power must be higher that the efficacy threshold after absorbance. The graph in FIG. 9B depicts an effect of light diffused from the light diffusing optical fiber 620 through a first absorption layer 622 and a second absorption layer 624. As light diffuses in a generally circularly symmetric fashion outwardly from the light diffusing optical fiber the power drops off at approximately $1/r^2$ in air. However, when the diffused light propagates through absorption layers 622 and 624 the diffused light power may decrease more depending on the material the diffused light propagates through.

Figure 10A:
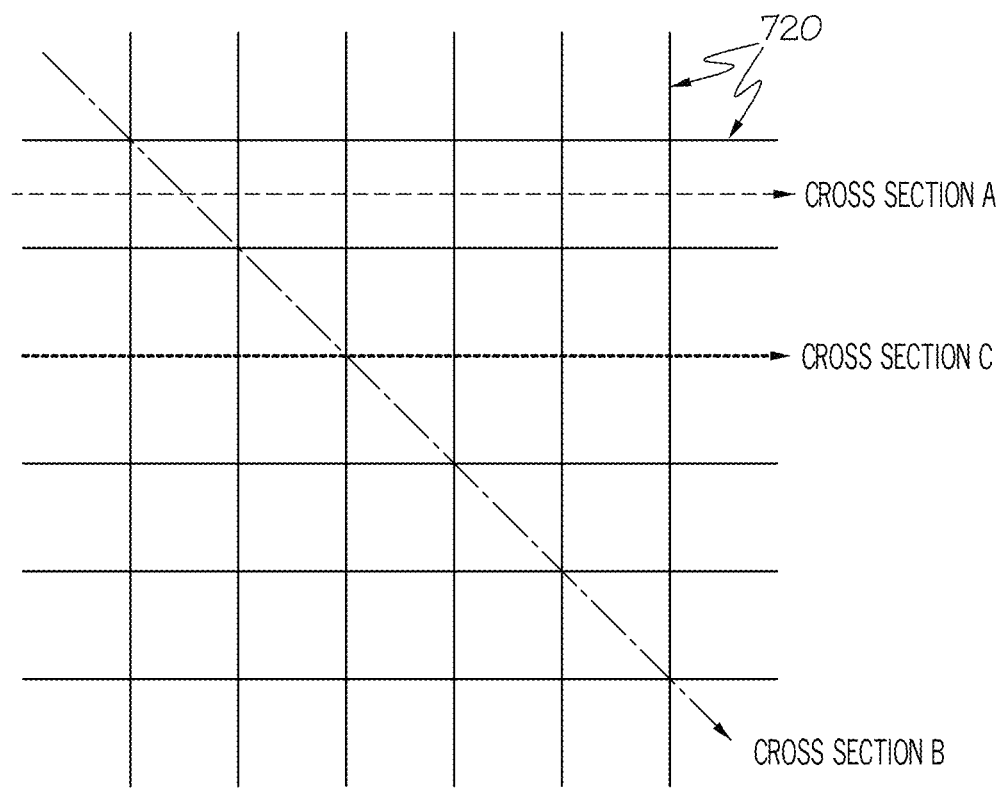
FIG. 10A schematically depicts a structured light diffusing optical fiber configuration according to one or more embodiments shown and described herein.
Figure 10B:
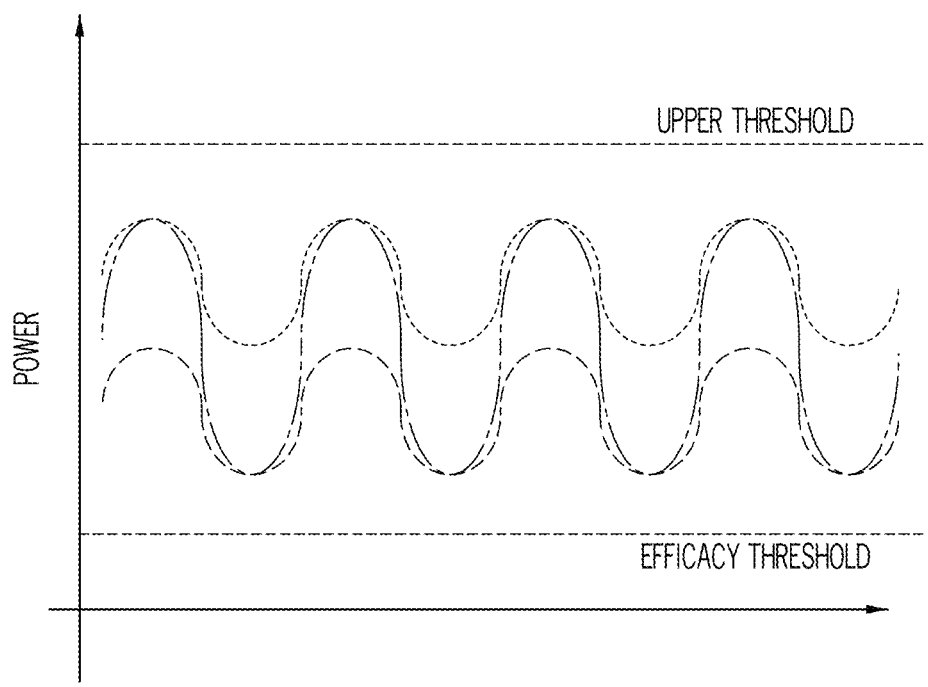
FIG. 10B graphically depicts power along various cross-sections of the structured light diffusing optical fiber configuration according to one or more embodiments shown and described herein.
Figure 10C:
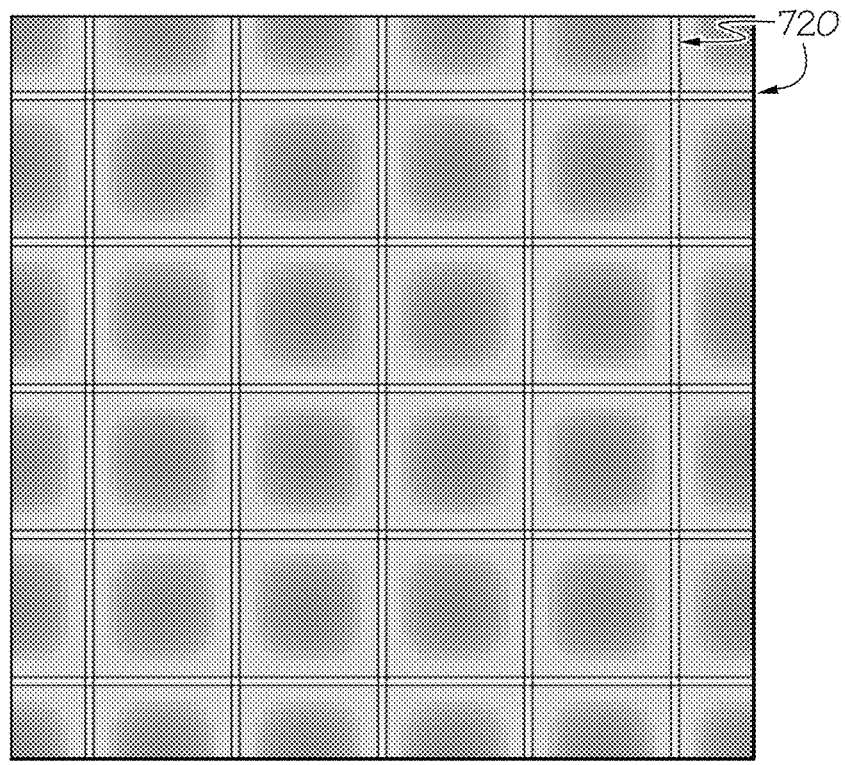
FIG. 10C depicts a heat map of a structured light diffusing optical fiber configuration according to one or more embodiments shown and described herein.
Figure 10D:
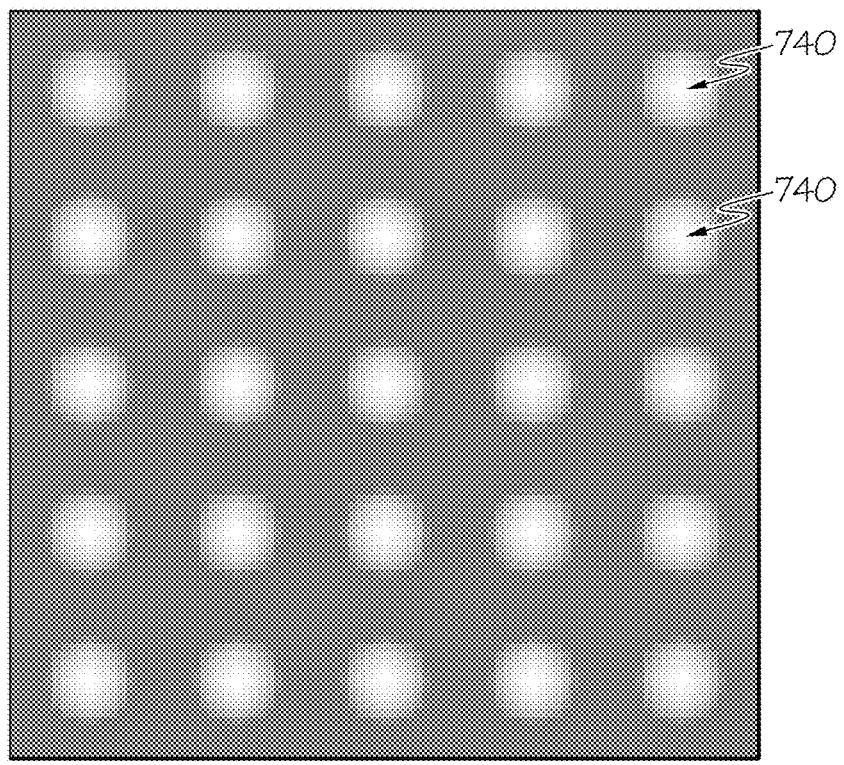
FIG. 10D depicts a heat map of a multiple point source light emitting diode configuration according to one or more embodiments shown and described herein.

Turning now to FIGS. 10A-10D, an example structured configuration is depicted. In some embodiments, such as the ones utilized in the following experimental examples, one or more light diffusing optical fibers may be configured in a structured fashion to create a plane or 3-D shape for a more uniform dispersion of diffused light above the efficacy threshold for disinfecting purposes. As shown in FIG. 10A, a light diffusing optical fiber 720 is configured in a woven gird structure. For purposes of discussion three cross-sectional planes are identified. Cross Section A is positioned along a midpoint of a row intersecting multiple columns. Cross Section B is positioned along light diffusing optical fiber row intersecting multiple columns. Cross Section C is positioned to traverse the rows and columns of the grid at an angle. FIG. 10B depicts the resulting power intensities of the diffused light across the structured configuration. Similarly, FIG. 10C depicts the same in the form of a heat map. As shown in FIG. 10C, diffused light may be configured to be dispersed more uniformly on a larger scale than multiple point source LEDs 740 in a similar grid structure configuration as shown in FIG. 10D.

It is contemplated that other structured configurations may be implemented without deviating from the spirit and scope of the present disclosure.

Experimental

Figure 11A:
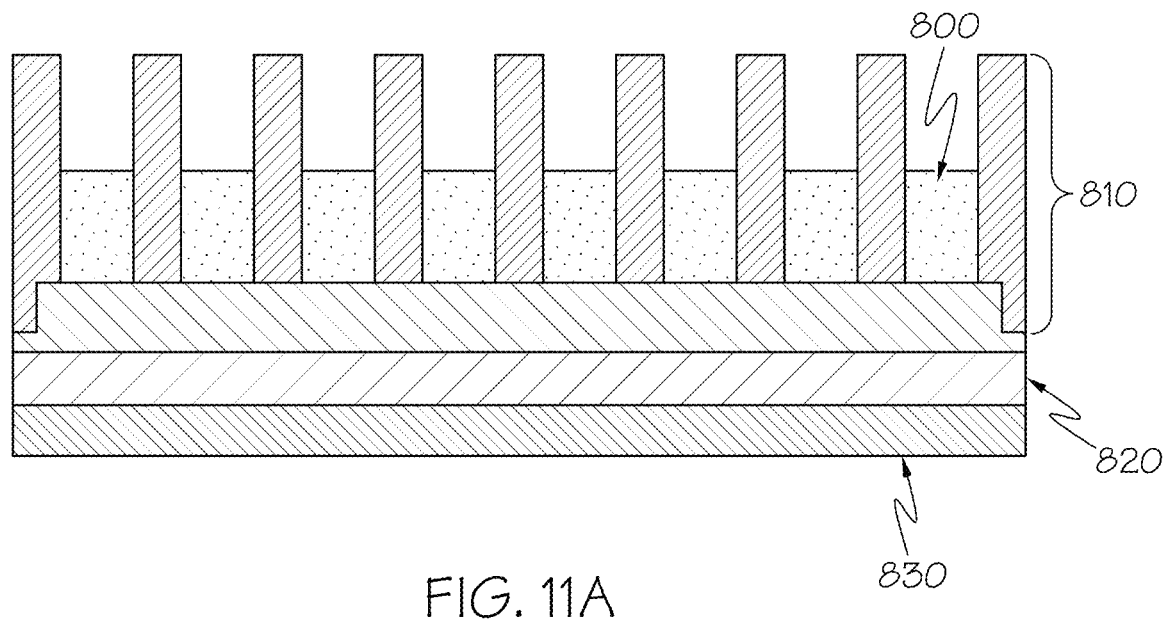
FIG. 11A schematically depict a configuration using a light diffusing optical fiber to disinfect according to one or more embodiments shown and described herein.

In a first experimental configuration, as shown in FIG. 11A, a pathogen sample 600 was seeded and grown in solution in a 96-well-plate 610. A light diffusing optical fiber 620 was configured parallel to the 96-well-plate 610 where a portion of light diffusing optical fiber illuminated each of the 96-wells with 405 nm light. Additionally, a reflective surface 630 was included such that the light diffusing optical fiber 620 was positioned between the 96-well-plate 610 and the reflective surface 630. It is understood that a "network" of one or more light diffusing optical fibers 620 may be configured in a parallel stand pattern, a crisscrossing pattern, a spiral formation, or other configuration within the flexible structural constraints of the light diffusing optical fiber. The power density of light emanating from the light diffusing optical fibers 620 was from about 7.2 mW/cm$^2$ to about 11.25 mW/cm$^2$ for exposure times from about 4 hours to about 24 hours. This yielded a total energy density of about 103 J/cm$^2$ to about 972 J/cm$^2$ being delivered to the pathogen samples in the 96-well-plate 610. The result of exposing approximately 1×10$^4$ CFUs of the pathogen sample 600 with said total energy density was a bactericidal effect of about a 4 Log to about a 6 Log reduction, e.g., from about 10,000 times to about 1,000,000 times fewer CFUs.

Figure 11B:
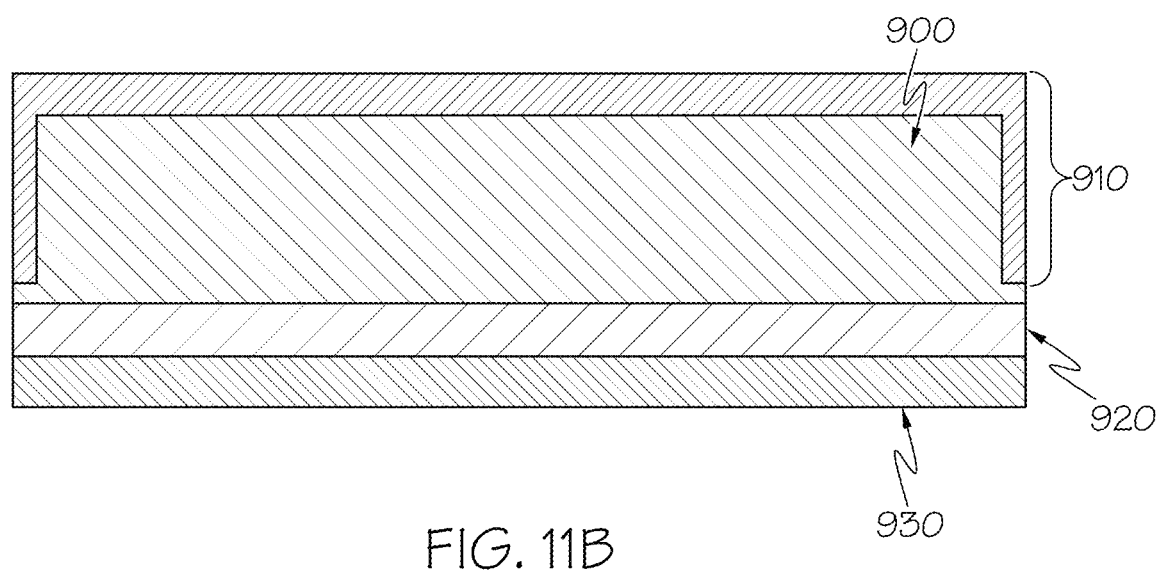
FIG. 11B schematically depict a configuration using a light diffusing optical fiber to disinfect according to one or more embodiments shown and described herein.

In a second experimental configuration, as shown in FIG. 11B, a pathogen sample 700 was seeded and grown on agar in a petri dish 710. A network of light diffusing optical fiber 720 was configured parallel to the petri dish 710 where the light diffusing optical fiber illuminated the pathogen sample 700 on the agar of the petri dish 710 with 405 nm light. Additionally, a reflective surface 730 was included such that the light diffusing optical fiber 720 was positioned between the pathogen sample 700 on the agar of the petri dish 710 and the reflective surface 730. The power density of light emanating from the light diffusing optical fibers 720 was from about 7.2 mW/cm$^2$ to about 11.25 mW/cm$^2$ for an exposure time of about 6 hours. This yielded a total energy density of about 155 J/cm$^2$ to about 243 J/cm$^2$ being delivered to the pathogen sample 700 on the agar. The result of exposing approximately 1×10$^9$ CFUs of the pathogen sample 700 with said total energy density was a bactericidal effect of about a 8 Log to about 9 Log reduction, e.g., from about 100,000,000 times to about 1,000,000,000 times fewer CFUs.

Three variations of gram-positive pathogen samples, i.e., *Staphylococcus aureus, Staphylococcus epidermidis*, and *Streptococcus pyogenes*, were tested in the above described experimental trials. In other trials, at least a 4 Log reduction efficacy was observed with both gram-positive pathogen samples, for example, without limitation, *C. albicans, S. pyogenes*, and *E. faecium* and gram-negative pathogen samples, for example, *P. aeruginosa, E. coli, A. baumannii, K. pneumoniae*, and *E. aerogenes*.

It should now be understood that the continuous application of 405 nm light from a light diffusing optical fiber to a pathogen sample or pathogen growth medium may provide continual disinfection by continually adding energy to a the pathogen sample or pathogen growth medium. It should also be understood, that visible, blue-violet light, e.g., 405 nm light, does not cause damage like UV light is known to with respect to human and pathogen cells. Additionally, it is understood that by using light diffusing optical fibers to deliver visible, blue-violet light, light may be delivered to hard-to-reach locations enabling a direct application to the source of potential or current pathogen growth and infection sites. One example, may be infections related to indwelling or percutaneous catheters, i.e., catheters that are partially inside and partially outside the body. As a result, pathogens may grow along and within a catheter thus delivering a direct path for infection within the body which may start from outside the body and proceed inward using the catheter as a medium for growth. Other examples may include disinfecting a cardiovascular catheter, an endotracheal tube, a Foley catheter, or the like.

In two different testing setups (a 96 well plate testing setup and an agar dish) were used to measure the effective power density and exposure time of the light delivery systems described herein with respect to various pathogens listed in Table 1. In the 96 well plate configuration, the bottom of the plate is blackened with the exception of the bottoms of each of the 96 wells. In the agar surface/petri dish configuration, there is no material between the fiber and the bacteria (except air), however this distance is greater than the distance between the fiber and the bottom of the 96 well plate.

TABLE 1

Measured antimicrobial effect.

| Species | Treatment Time (hr) | Viability Reduction (Log$_{10}$)[1] | | |
| --- | --- | --- | --- | --- |
| | | 25 mW/cm$^2$ | 10 mW/cm$^2$ | 5 mW/cm$^2$ |
| *Enterococcus faecium* | 2 | — | — | — |
| | 4 | ≤10$^4$ | — | — |
| | 6 | 10$^4$ | — | — |
| *Staphylococcus aureus* | 2 | 10$^4$ | — | — |
| | 4 | 10$^6$ | 10$^4$ | — |
| | 6 | 10$^6$ | 10$^6$ | ≤10$^4$ |

TABLE 1-continued

Measured antimicrobial effect.

| Species | Treatment Time (hr) | 25 mW/cm² | 10 mW/cm² | 5 mW/cm² |
|---|---|---|---|---|
| Klebsiella pneumoniae | 2 | — | — | — |
|  | 4 | ≤$10^4$ | ≤$10^4$ | — |
|  | 6 | $10^5$ | $10^4$ | ≤$10^4$ |
| Acinetobacter baumannii | 2 | $10^4$ | — | — |
|  | 4 | $10^4$ | $10^4$ | — |
|  | 6 | $10^4$ | ≤$10^4$ | ≤$10^4$ |
| Pseudomonas aeruginosa | 2 | $10^7$ | $10^6$ | ≤$10^4$ |
|  | 4 | $10^6$ | $10^6$ | ≤$10^4$ |
|  | 6 | $10^7$ | $10^6$ | ≤$10^4$ |
| Enterobacter sp. | 2 | ≤$10^4$ | — | — |
|  | 4 | $10^5$ | ≤$10^4$ | — |
|  | 6 | $10^5$ | ≤$10^4$ | — |
| Streptococcus pyogenes | 2 | ≤$10^8$ | ≤$10^8$ | ≤$10^8$ |
|  | 4 | ≤$10^8$ | ≤$10^8$ | ≤$10^8$ |
|  | 6 | ≤$10^8$ | ≤$10^8$ | ≤$10^8$ |
| Candida albicans | 2 | ≤$10^4$ | ≤$10^4$ | — |
|  | 4 | $10^6$ | ≤$10^4$ | ≤$10^4$ |
|  | 6 | ≤$10^7$ | $10^6$ | ≤$10^4$ |
| Escherichia coli | 2 | ≤$10^4$ | — | — |
|  | 4 | $10^5$ | ≤$10^4$ | — |
|  | 6 | $10^6$ | $10^5$ | ≤$10^4$ |
| Staph. aureus ΔhemB | 2 | — | — | — |
|  | 4 | ≤$106$ | ≤$104$ | — |
|  | 6 | $10^7$ | $10^7$ | ≤$10^4$ |

[1]≤$10^X$ indicates more than 50% reduction in the indicated inoculum; (—) indicates less than 50% or no measurable reduction in $10^4$ inoculum.

TABLE 2

Fluence[1] required for significant[2] antimicrobial effect

| Species | Fluence (J/cm²) |
|---|---|
| Enterococcus faecium | 540 |
| Staphylococcus aureus | 144 |
| Klebsiella pneumoniae | 144 |
| Acinetobacter baumannii | 144 |
| Pseudomonas aeruginosa | 72 |
| Enterobacter sp. | 360 |
| Streptococcus pyogenes | 363 |
| Candida albicans | 216 |
| Escherichia coli | 216 |
| Staph. aureus ΔhemB | 216 |

[1]Radiant energy measured in Joules (J/cm²).
[2]Greater than or equal to a 4-$\log_{10}$ reduction in organism viability.
[3] As noted above, no doses completely eradicated the organism, regardless of inoculum size.

As shown in Table 1, the minimum effective energy densities range from 36 mJ/cm² to about 540 mJ/cm². The range of power densities tested was 5 mW/cm², 10 mW/cm² and 25 mW/cm², the range of exposure times was 2, 4 or 6 hours, and the range of concentrations tested was $10^4$-$10^8$ CFU/mL. All exposures were continuous wave.

Aspect (1) pertains to a method of disinfecting using a blue-violet light delivery system comprising: optically coupling a light source to a blue-violet light delivery system; positioning the blue-violet light delivery system in optical engagement with a pathogen sample; and directing light output by the light source into the blue-violet light delivery system for a first time interval thereby irradiating the pathogen sample with light comprising an average power density of about 5 mW/cm² to about 30 mW/cm² at a wavelength from about 380 nm to about 495 nm for an exposure time from about 30 minutes to about 48 hours.

Aspect (2) pertains to the method of Aspect (1), wherein the blue-violet light delivery system comprises one or more light diffusing optical fibers comprising: a core; a cladding surrounding the core; an outer surface; and a plurality of scattering structures positioned within the core, the cladding, or both the core and the cladding.

Aspect (3) pertains to the method of Aspect (1), wherein, when the light output is directed by the light source into the blue-violet light delivery system, the plurality of scattering structures of the one or more light diffusing optical fibers scatter light propagating along the one or more light diffusing optical fibers toward the outer surface and a portion of light diffuses through the outer system.

Aspect (4) pertains to the method of any one of Aspects (1) through (3), wherein the average power density is from about 7.2 mW/cm² to about 11.25 mW/cm².

Aspect (5) pertains to the method of any one of Aspects (1) through (4), wherein the exposure time is from about 2 hours to about 8 hours.

Aspect (6) pertains to the method of any one of Aspects (1) through (5), wherein the exposure time is from about 4 hours to about 24 hours.

Aspect (7) pertains to the method of any one of Aspects (1) through (6), wherein the light output by the light source into the blue-violet light delivery system is pulsed.

Aspect (8) pertains to the method of Aspect (7), wherein: the light source is configured to output pulsed light in a first pulse cycle and a second pulse cycle; one or more pulses output by the light source in the first pulse cycle comprise a first pulse duration; and one or more pulses output by the light source in the second pulse cycle comprise a second pulse duration.

Aspect (9) pertains to the method of Aspect (8), wherein the first pulse duration is greater than the second pulse duration.

Aspect (10) pertains to the method of any one of Aspects (1) through (9), further comprising directing light output by the light source into the blue-violet light delivery system for a second time interval, wherein an energy density during the second time interval is less than an energy density during the first time interval.

Aspect (11) pertains to the method of any one of Aspects (1) through (10), wherein the pathogen sample is a gram-positive pathogen.

Aspect (12) pertains to the method of Aspect (11), wherein the gram-positive pathogen is at least one of *Staphylococcus aureus, Staphylococcus epidermidis, Candida albicans, Streptococcus pyogenes,* and *Enterococcus faecium.*

Aspect (13) pertains to the method of any one of Aspects (2) through (12), wherein the core comprises glass doped with 300 ppm or more of a hydroxyl material and the cladding comprises glass doped with 300 ppm or more of a hydroxyl material.

Aspect (14) pertains to the method of any one of Aspects (2) through (13), wherein a thermoplastic polymer coating layer surrounds and contacts the cladding.

Aspect (15) pertains to the method of any one of Aspects (2) through (14), wherein a primary coating layer surrounds the cladding, and a thermoplastic polymer coating layer surrounds the primary coating layer such that the primary coating layer is disposed between the cladding and the thermoplastic polymer coating layer, the primary coating layer comprises a cycloaliphatic epoxy having an absorbance of about 0.04 or less per 100 μm of layer thickness at a wavelength of about 250 nm or more.

Aspect (16) pertains to the method of any one of Aspects (2) through (15), wherein a coating layer surrounds the cladding and the coating layer is doped with a plurality of scattering structures.

Aspect (17) pertains to the method of any one of Aspects (1) through (16), wherein the light source is linearly polarized.

Aspect (18) pertains to the method of any one of Aspects (1) through (17), wherein the light source is a laser diode.

Aspect (19) pertains to a method of disinfecting using a blue-violet light delivery system comprising: optically coupling a light source to the blue-violet light delivery system positioning the blue-violet light delivery system in optical engagement with a pathogen sample; directing light output by the light source into the blue-violet light delivery system for a first time interval thereby irradiating the pathogen sample comprising an amount of colony forming units with light comprising an average power density of about 5 mW/cm$^2$ to about 30 mW/cm$^2$ at a wavelength from about 380 nm and about 495 nm, wherein the amount of colony forming units of the pathogen sample are reduced by about a 4-Log reduction to about a 9-Log reduction.

Aspect (20) pertains to the method of Aspect (19), wherein the blue-violet light delivery system comprises one or more light diffusing optical fibers comprising: a core; a cladding surrounding the core; an outer surface; and a plurality of scattering structures positioned within the core, the cladding, or both the core and the cladding;

Aspect (21) pertains to the method of Aspect (20), wherein, when the light output is directed by the light source into the blue-violet light delivery system, the plurality of scattering structures of the one or more light diffusing optical fibers scatter light propagating along the one or more light diffusing optical fibers toward the outer surface and a portion of light diffuses through the outer system.

Aspect (22) pertains to the method of any one of Aspects (19) through (21), wherein the average power density is from about 7.2 mW/cm$^2$ to about 11.25 mW/cm$^2$.

Aspect (23) pertains to the method of any one of Aspects (19) through (22), wherein an exposure time of the light on the pathogen sample is from about 2 hours to about 24 hours.

Aspect (24) pertains to the method of any one of Aspects (19) through (23), wherein an exposure time of the light on the pathogen sample is from about 2 hours to about 8 hours.

Aspect (25) pertains to the method of any one of Aspects (19) through (24), wherein the light output by the light source into the blue-violet light delivery system is pulsed.

Aspect (26) pertains to the method of Aspect (25), wherein: the light source is configured to output pulsed light in a first pulse cycle and a second pulse cycle; one or more pulses output by the light source in the first pulse cycle comprise a first pulse duration; and one or more pulses output by the light source in the second pulse cycle comprise a second pulse duration.

Aspect (27) pertains to the method of Aspect (26), wherein the first pulse duration is greater than the second pulse duration.

Aspect (28) pertains to the method of any one of Aspects (19) through (27), further comprising directing light output by the light source into the blue-violet light delivery system for a second time interval, wherein an energy density during the second time interval is less than an energy density during the first time interval.

Aspect (29) pertains to the method of any one of Aspects (19) through (28), wherein the pathogen sample is a gram-positive pathogen.

Aspect (30) pertains to the method of Aspect (29), wherein the gram-positive pathogen is at least one of *Staphylococcus aureus, Staphylococcus epidermidis, Candida albicans, Streptococcus pyogenes,* and *Enterococcus faecium.*

Aspect (31) pertains to the method of any one of Aspects (19) through (28), wherein the pathogen sample is a gram-negative pathogen.

Aspect (32) pertains to the method of Aspect (31), wherein the gram-negative pathogen is at least one of *Pseudomonas aeruginosa, Escherichia coli, Acinetobacter baumannii, Klebsiella pneumoniae,* and *Enterobacter aerogenes.*

Aspect (33) pertains to the method of any one of Aspects (20) through (32), wherein the core comprises glass doped with 300 ppm or more of a hydroxyl material and the cladding comprises glass doped with 300 ppm or more of a hydroxyl material.

Aspect (34) pertains to the method of any one of Aspects (20) through (33), wherein a thermoplastic polymer coating layer surrounds and contacts the cladding.

Aspect (35) pertains to the method of any one of Aspects (20) through (34), wherein a primary coating layer surrounds the cladding, and a thermoplastic polymer coating layer surrounds the primary coating layer such that the primary coating layer is disposed between the cladding and the thermoplastic polymer coating layer, the primary coating layer comprises a cycloaliphatic epoxy having an absorbance of about 0.04 or less per 100 μm of layer thickness at a wavelength of about 250 nm or more.

Aspect (36) pertains to the method of any one of Aspects (20) through (35), wherein a coating layer surrounds the cladding and the coating layer is doped with a plurality of scattering structures.

Aspect (37) pertains to a light delivery system for delivering blue-violet light comprising: a blue-violet light irradiating device that emits a light comprising an average power density of about 5 mW/cm$^2$ to about 30 mW/cm$^2$ at a wavelength from about 380 nm to about 495 nm, wherein after a pathogen sample comprising an amount of colony forming units is irradiated with the light for an exposure time from about 30 minutes to about 48 hours, the amount of colony forming units of the pathogen sample are reduced by about a 4-Log reduction to about a 9-Log reduction.

Aspect (38) pertains to the system of Aspect (37), wherein the average power density is from about 7.2 mW/cm$^2$ to about 11.25 mW/cm$^2$.

Aspect (39) pertains to the system of Aspect (37) or Aspect (38), wherein the exposure time is from about 2 hours to about 8 hours.

Aspect (40) pertains to the system of any one of Aspects (37) through (39), wherein the exposure time is from about 4 hours to about 24 hours.

Aspect (41) pertains to the system of any one of Aspects (37) through (40), wherein the light is pulsed.

Aspect (42) pertains to the system of Aspect (41), wherein: the light is pulsed according to a first pulse cycle and a second pulse cycle; wherein the first pulse cycle comprises a first pulse duration, and wherein the second pulse cycle comprises a second pulse duration.

Aspect (43) pertains to the system of Aspect (42), wherein the first pulse duration is greater than the second pulse duration.

Aspect (44) pertains to the system of any one of Aspects (37) through (43), wherein the pathogen sample is a gram-positive pathogen.

Aspect (45) pertains to the system of Aspect (44), wherein the gram-positive pathogen is at least one of *Staphylococcus aureus, Staphylococcus epidermidis, Candida albicans, Streptococcus pyogenes,* and *Enterococcus faecium.*

Aspect (46) pertains to the system of any one of Aspects (37) through (45), further comprising a light source optically connected to the light irradiating device, wherein the light source is linearly polarized.

Aspect (47) pertains to the system of any one of Aspects (37) through (46), further comprising a light source optically connected to the light irradiating device, wherein the light source is a laser diode.

Aspect (48) pertains to a light delivery system for disinfection comprising: a light irradiating device for irradiating a pathogen with a light in vivo, ex vivo or both in vivo and ex vivo, wherein the pathogen comprising an amount of colony forming units, wherein the light comprising an average power density of about 5 mW/cm$^2$ to about 30 mW/cm$^2$ at a wavelength from about 380 nm to about 495 nm, and wherein when the pathogen is irradiated with the light for an exposure time from about 30 minutes to about 48 hours, the amount of colony forming units of the pathogen sample are reduced by about a 4-Log reduction to about a 9-Log reduction.

Aspect (49) pertains to the system of Aspect (48), wherein the light irradiating device is positioned at a distance of about 30 mm or less from the pathogen.

Aspect (50) pertains to the system of Aspect (49), wherein the light irradiating device is positioned at a distance from about 2 mm to about 30 mm or less from the pathogen.

Aspect (51) pertains to the system of Aspect (49), wherein the light irradiating device is in contact with the pathogen.

Aspect (52) pertains to the system of any one of Aspects (48) through (51), wherein light irradiating device is positioned at a distance from about 2 mm to about 30 mm or less from the pathogen.

Aspect (53) pertains to the system of any one of Aspects (48) through (52), wherein the light is pulsed.

Aspect (54) pertains to the system of any one of Aspects (48) through (53), wherein the pathogen is a gram-positive pathogen.

Aspect (55) pertains to the system of Aspect (49), wherein the gram-positive pathogen is at least one of *Staphylococcus aureus, Staphylococcus epidermidis, Candida albicans, Streptococcus pyogenes,* and *Enterococcus faecium.*

Aspect (56) pertains to the system of any one of Aspects (48) through (53), wherein the pathogen is a gram-negative pathogen.

Aspect (57) pertains to the system of Aspect (56), wherein the gram-negative pathogen is at least one of *Pseudomonas aeruginosa, Escherichia coli, Acinetobacter baumannii, Klebsiella pneumoniae,* and *Enterobacter aerogenes.*

Aspect (58) pertains to the system of any one of Aspects (48) through (53), wherein, when the pathogen is *Enterococcus faecium,* and after pathogen is irradiated with the light having an average power density 25 mW/cm$^2$ for an exposure time of about 6 hours, the amount of colony forming units of the pathogen sample are reduced by about a 4-Log reduction or greater.

Aspect (59) pertains to the system of any one of Aspects (48) through (53), wherein, when the pathogen is *Staphylococcus aureus,* and after pathogen is irradiated with the light having an average power density 10 mW/cm$^2$ for an exposure time of about 4 hours or with the light having a power density of 25 mW/cm$^2$ for an exposure time of about 2 hours, the amount of colony forming units of the pathogen sample are reduced by about a 4-Log reduction or greater.

Aspect (60) pertains to the system of any one of Aspects (48) through (53), wherein, when the pathogen is *Klebsiella pneumoniae,* and after pathogen is irradiated with the light having an average power density 10 mW/cm$^2$ for an exposure time of about 6 hours, the amount of colony forming units of the pathogen sample are reduced by about a 4-Log reduction or greater.

Aspect (61) pertains to the system of any one of Aspects (48) through (53), wherein, when the pathogen is *Acinetobacter baumannii,* and after pathogen is irradiated with the light having an average power density 10 mW/cm$^2$ for an exposure time of about 4 hours or with the light having a power density of 25 mW/cm$^2$ for an exposure time of about 2 hours, the amount of colony forming units of the pathogen sample are reduced by about a 4-Log reduction or greater.

Aspect (62) pertains to the system of any one of Aspects (48) through (53), wherein, when the pathogen is *Pseudomonas aeruginosa,* and after pathogen is irradiated with the light having an average power density 10 mW/cm$^2$ for an exposure time of about 2, the amount of colony forming units of the pathogen sample are reduced by about a 4-Log reduction or greater.

Aspect (63) pertains to the system of any one of Aspects (48) through (53), wherein, when the pathogen is *Streptococcus pyogenes,* and after pathogen is irradiated with the light having an average power density 5 mW/cm$^2$ for an exposure time of about 2, the amount of colony forming units of the pathogen sample are reduced by about a 4-Log reduction or greater.

Aspect (64) pertains to the system of any one of Aspects (48) through (53), wherein, when the pathogen is *Candida albicans,* and after pathogen is irradiated with the light having an average power density 10 mW/cm$^2$ for an exposure time of about 6 or with the light having a power density of 25 mW/cm$^2$ for an exposure time of about 4 hours, the amount of colony forming units of the pathogen sample are reduced by about a 4-Log reduction or greater.

Aspect (65) pertains to the system of any one of Aspects (48) through (53), wherein, when the pathogen is *Escherichia coli,* and after pathogen is irradiated with the light having an average power density 10 mW/cm$^2$ for an exposure time of about 6 or with the light having a power density of 25 mW/cm$^2$ for an exposure time of about 4 hours, the amount of colony forming units of the pathogen sample are reduced by about a 4-Log reduction or greater.

For the purposes of describing and defining the present technology, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters. Another example may include configuring one or more light diffusing fibers within or between a bandage and a wound to provide disinfecting light treatment directly to the wound without exposing the wound to infectious environments.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" in a particular way, to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present technology it is noted that the terms "substantially" and "about" are utilized herein to represent the inherent degree of uncertainty that may be attributed to any quantitative comparison, value, measurement, or other representation. The terms "substantially" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A method of disinfecting using a blue-violet light delivery system comprising:
    optically coupling a light source to a blue-violet light delivery system;
    positioning the blue-violet light delivery system in optical engagement with a pathogen sample; and
    directing light output by the light source into the blue-violet light delivery system for a first time interval thereby irradiating the pathogen sample with light comprising an average power density of about 5 mW/cm$^2$ to about 30 mW/cm$^2$ at a wavelength from about 380 nm to about 495 nm for an exposure time from about 30 minutes to about 48 hours,
    wherein the blue-violet light delivery system
    comprises one or more light diffusing optical fibers comprising:
        (a) a core;
        (b) a cladding surrounding the core; an outer surface;
        (c) a plurality of scattering structures positioned within the core, the cladding, or both the core and the cladding; wherein the core comprises glass doped with 300 ppm or more of a hydroxyl material and the cladding comprises glass doped with 300 ppm or more of a hydroxyl material; and
        (d) a coating layer comprising a cycloaliphatic epoxy having an absorbance of about 0.04 or less per 100 μm of layer thickness at a wavelength of about 250 nm or more.

2. The method of claim 1, wherein, when the light output is directed by the light source into the blue-violet light delivery system, the plurality of scattering structures of the one or more light diffusing optical fibers scatter light propagating along the one or more light diffusing optical fibers toward the outer surface and a portion of light diffuses through the outer surface.

3. The method of claim 1, wherein the average power density is from about 7.2 mW/cm$^2$ to about 11.25 mW/cm$^2$.

4. The method of claim 1, wherein a thermoplastic polymer coating layer surrounds and contacts the cladding.

5. The method of claim 1, wherein a coating layer surrounds the cladding and the coating layer is doped with a plurality of scattering structures.

6. The method of disinfecting using a blue-violet light delivery system according to claim 1
    wherein the amount of colony forming units of the pathogen sample are reduced by about a 4-Log reduction to about a 9-Log reduction.

7. A method of disinfecting using a blue-violet light delivery system comprising:
    optically coupling a light source to a blue-violet light delivery system;
    positioning the blue-violet light delivery system in optical engagement with a pathogen sample; and
    directing light output by the light source into the blue-violet light delivery system for a first time interval thereby irradiating the pathogen sample with light comprising an average power density of about 5 mW/cm$^2$ to about 30 mW/cm$^2$ at a wavelength from about 380 nm to about 495 nm for an exposure time from about 30 minutes to about 48 hours,
    wherein the blue-violet light delivery system
    comprises one or more light diffusing optical fibers comprising:
        a core;
        a cladding surrounding the core; an outer surface; and
        a plurality of scattering structures positioned within the core, the cladding, or both the core and the cladding;
    wherein the core comprises glass doped with 300 ppm or more of a hydroxyl material and the cladding comprises glass doped with 300 ppm or more of a hydroxyl material
    wherein a primary coating layer surrounds the cladding, and a thermoplastic polymer coating layer surrounds the primary coating layer such that the primary coating layer is disposed between the cladding and the thermoplastic polymer coating layer, the primary coating layer comprises a cycloaliphatic epoxy having an absorbance of about 0.04 or less per 100 μm of layer thickness at a wavelength of about 250 nm or more.

8. The method of claim 7, wherein, when the light output is directed by the light source into the blue-violet light delivery system, the plurality of scattering structures of the one or more light diffusing optical fibers scatter light propagating along the one or more light diffusing optical fibers toward the outer surface and a portion of light diffuses through the outer surface.

* * * * *